United States Patent
Cable, II et al.

(10) Patent No.: US 12,193,972 B2
(45) Date of Patent: Jan. 14, 2025

(54) INTRAOCULAR DRUG DELIVERY SYSTEMS AND METHODS OF USE

(71) Applicants: SpyGlass Pharma, Inc., Aliso Viejo, CA (US); The Regents of the University of Colorado, Denver, CO (US)

(72) Inventors: Craig Alan Cable, II, Aliso Viejo, CA (US); Malik Y. Kahook, Denver, CO (US); Ryan Absalonson, Aliso Viejo, CA (US); Glenn R. Sussman, Aliso Viejo, CA (US)

(*) Notice: Subject to any disclaimer, the term of this patent is extended or adjusted under 35 U.S.C. 154(b) by 0 days.

(21) Appl. No.: 18/356,138

(22) Filed: Jul. 20, 2023

(65) Prior Publication Data

US 2024/0024092 A1    Jan. 25, 2024

Related U.S. Application Data

(63) Continuation of application No. PCT/US2023/070625, filed on Jul. 20, 2023.

(60) Provisional application No. 63/500,231, filed on May 4, 2023, provisional application No. 63/391,399, filed on Jul. 22, 2022.

(51) Int. Cl.
*A61F 9/00* (2006.01)
*A61F 2/16* (2006.01)
*A61F 9/007* (2006.01)

(52) U.S. Cl.
CPC .............. *A61F 9/0017* (2013.01); *A61F 2/16* (2013.01); *A61F 2/1601* (2015.04); *A61F 2002/1681* (2013.01); *A61F 2002/1689* (2013.01); *A61F 2002/16901* (2015.04); *A61F 2/1691* (2013.01);

(Continued)

(58) Field of Classification Search
CPC ........ A61F 2/16; A61F 2/1613; A61F 2/1648; A61F 2/1681; A61F 2002/1689; A61F 2002/16901; A61F 2250/0068; A61F 9/0008; A61F 9/0017
See application file for complete search history.

(56) References Cited

U.S. PATENT DOCUMENTS 10,667,947 B2    6/2020    Horvath et al.
11,298,262 B2    4/2022    Kahook et al.
(Continued)

OTHER PUBLICATIONS

Patent Cooperation Treaty, International Search Report and Written Opinion, International Application No. PCT/US2023/070625, date of mailing Jan. 19, 2024, 12 pages.
(Continued)

*Primary Examiner* — William H Matthews
(74) *Attorney, Agent, or Firm* — Polsinelli PC

(57) ABSTRACT

Embodiments of the instant disclosure relate to intraocular drug delivery devices for and methods of, delivering at least one therapeutic agent to an eye of a subject. Methods include implanting an intraocular implant into the eye and adjacent to a fluid-permeable membrane of the eye of the patient. Intraocular implants are supported in a position at a surface of the fluid-permeable membrane. Intraocular implants include a drug delivery component having at least one therapeutic agent embedded within a non-bioerodible, non-biodegradable polymer matrix. Devices and methods disclosed herein can further include delivering the at least one therapeutic agent to the eye of the subject according to a near zero-order elution rate of the at least one therapeutic agent.

23 Claims, 9 Drawing Sheets

(52) U.S. Cl.
CPC ....... *A61F 9/00781* (2013.01); *A61F 2210/00* (2013.01); *A61F 2250/0068* (2013.01)

(56) References Cited

U.S. PATENT DOCUMENTS

| | | | |
|---|---|---|---|
| 11,399,977 | B2 | 8/2022 | Dennewill et al. |
| 2007/0208134 | A1 | 9/2007 | Hunter et al. |
| 2010/0074942 | A1* | 3/2010 | Ratner ................. A61K 31/711 |
| | | | 29/282 |
| 2013/0062809 | A1 | 3/2013 | Ellis et al. |
| 2013/0245754 | A1 | 9/2013 | Blum et al. |
| 2015/0374541 | A1 | 12/2015 | de Juan, Jr. et al. |
| 2016/0287380 | A1 | 10/2016 | Shi et al. |
| 2016/0287513 | A1 | 10/2016 | Rakic et al. |
| 2017/0239176 | A1 | 8/2017 | Nair et al. |
| 2018/0228831 | A1 | 8/2018 | Larson et al. |
| 2018/0271704 | A1 | 9/2018 | Lifshitz et al. |
| 2018/0344763 | A1 | 12/2018 | Locock et al. |
| 2019/0117454 | A1* | 4/2019 | Campbell ............ A61K 9/0051 |
| 2019/0125581 | A1 | 5/2019 | Heitzmann et al. |
| 2020/0022840 | A1 | 1/2020 | Kahook et al. |
| 2020/0405538 | A1* | 12/2020 | Mandell .................. A61L 31/16 |
| 2021/0055217 | A1 | 2/2021 | Blackburn et al. |
| 2021/0267751 | A1 | 9/2021 | Sussman et al. |
| 2021/0322212 | A1* | 10/2021 | Adams .................. A61F 2/1694 |
| 2022/0168142 | A1 | 6/2022 | Saim et al. |
| 2022/0211800 | A1 | 7/2022 | Pena et al. |
| 2022/0389035 | A1 | 12/2022 | Hormann et al. |

OTHER PUBLICATIONS

U.S. Patent and Trademark Office, Non-Final Office Action, U.S. Appl. No. 18/356,122, dated Nov. 3, 2023, 15 pages.

U.S. Patent and Trademark Office, Non-Final Office Action, U.S. Appl. No. 18/356,122, Jul. 29, 2024, 25 pages.

U.S. Patent and Trademark Office, Notice of Allowance, U.S. Appl. No. 18/356,133, Aug. 8, 2024, 12 pages.

* cited by examiner

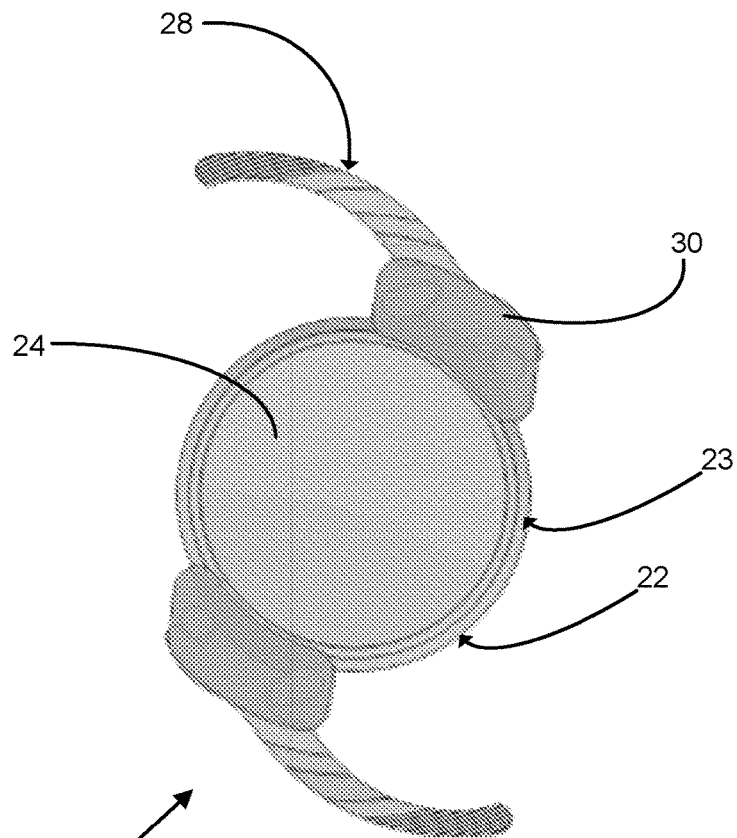
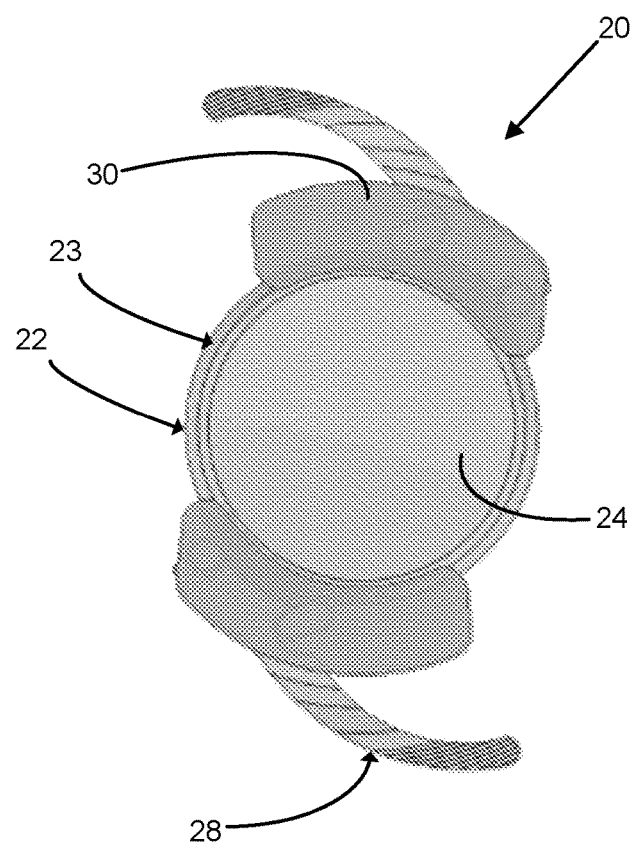
FIG. 3A
FIG. 3B

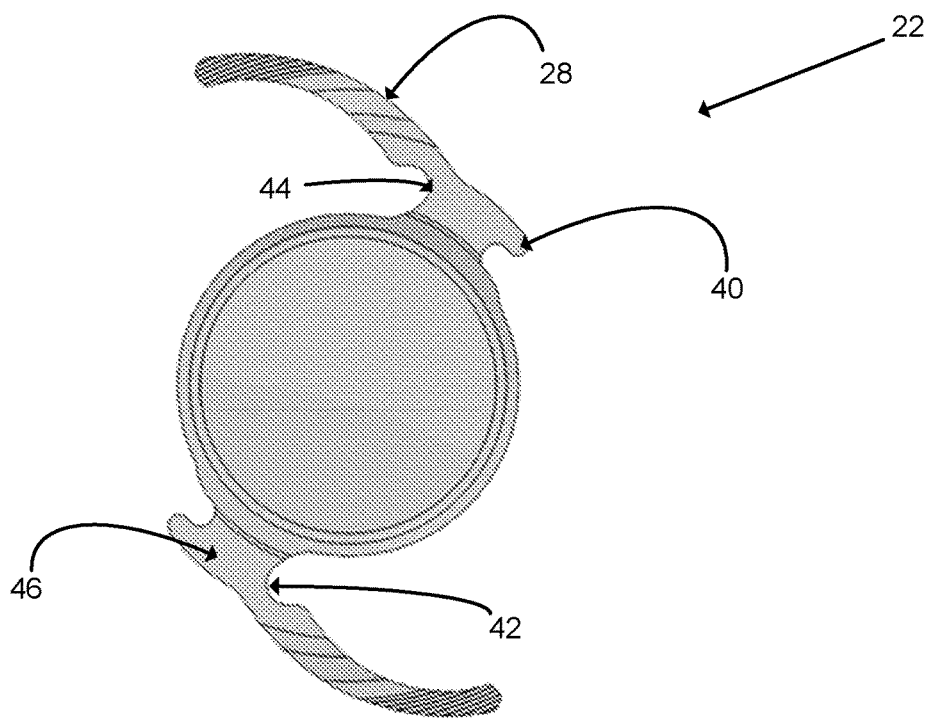
FIG. 4A
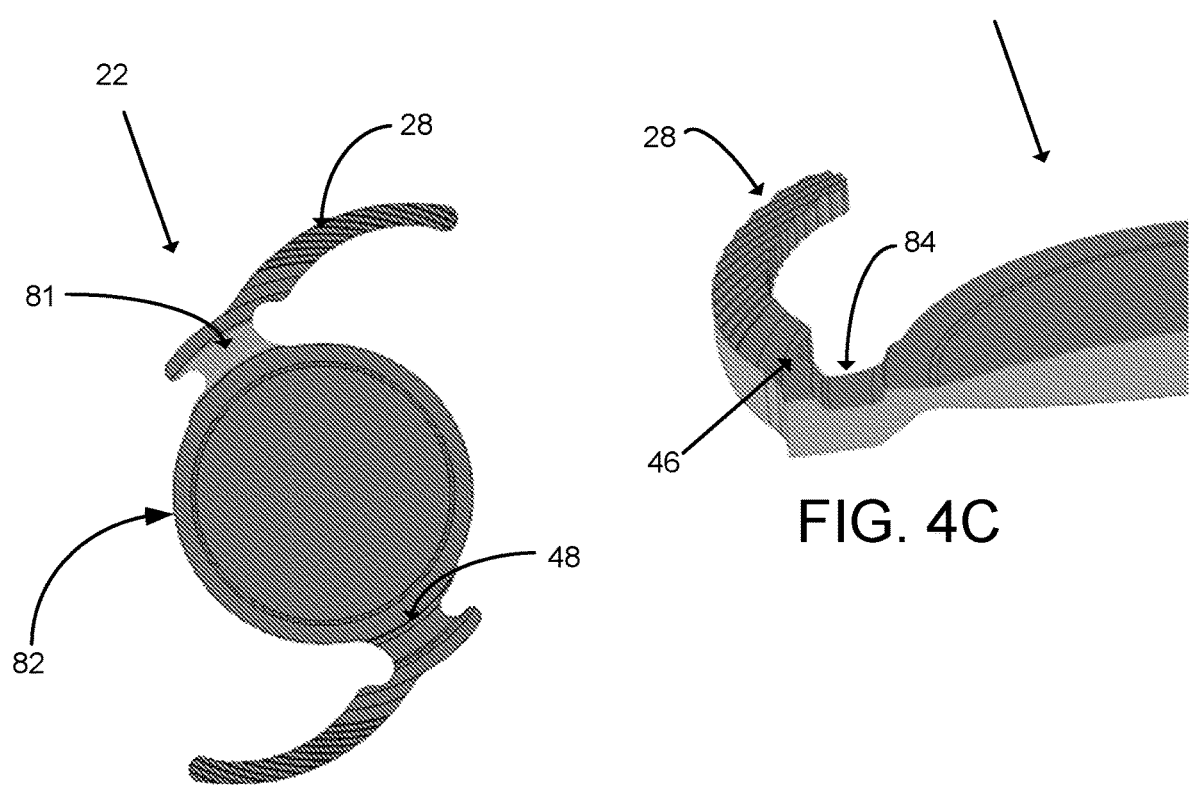
FIG. 4B
FIG. 4C

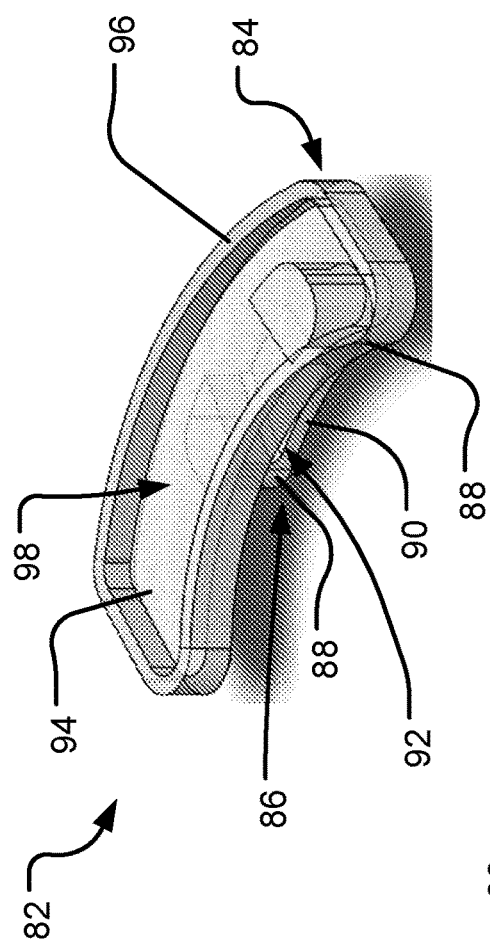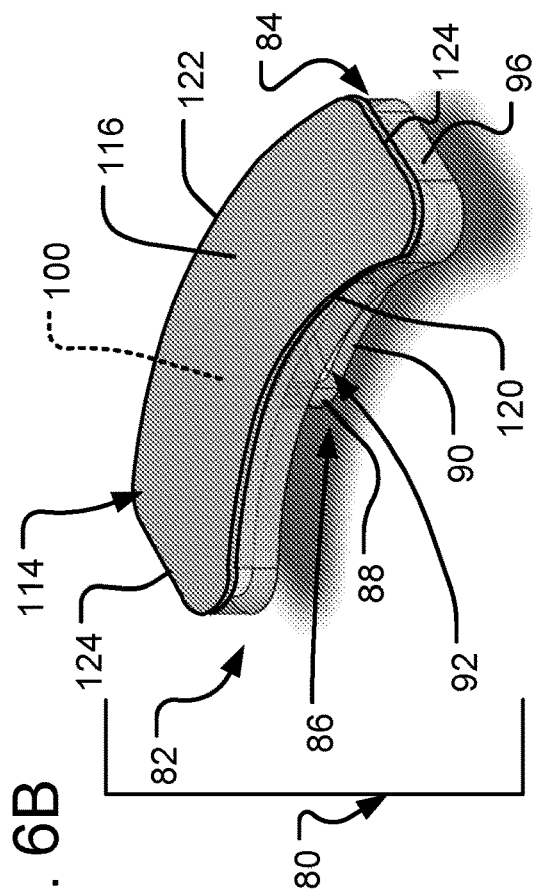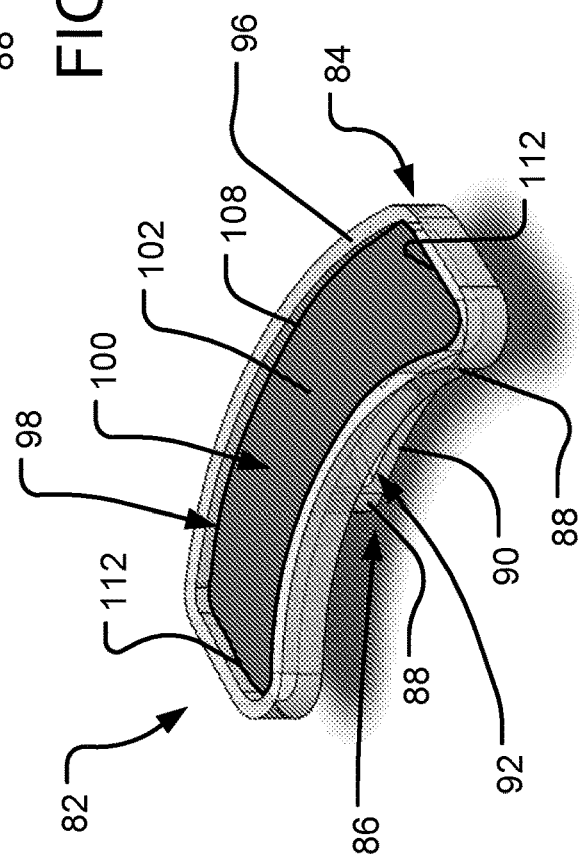

INTRAOCULAR DRUG DELIVERY SYSTEMS AND METHODS OF USE

CROSS-REFERENCE TO RELATED APPLICATIONS

This application is a continuation of International Application No. PCT/US2023/070625, filed Jul. 20, 2023, which claims the benefit of U.S. Provisional Application No. 63/500,231, filed May 4, 2023, and U.S. Provisional Application No. 63/391,399, filed Jul. 22, 2022, which are all incorporated herein by reference in their entireties for all purposes.

FIELD

The present disclosure relates to the field of intraocular drug delivery systems, pharmaceutical compositions, and methods of use thereof.

BACKGROUND

Intraocular lenses (IOLs) are artificial lenses for the eye that can be implanted to replace the natural lens of a patient's eye after the natural lens is removed. By way of example, a patient's natural lens can be removed because it is affected by cataracts, and an IOL can be implanted to provide clear vision and some degree of focusing for the patient. An intraocular lens can also be implanted in a patient without removing the natural lens (a phakic intraocular lens or PIOL), to correct extreme near-sightedness or far-sightedness.

In certain situations, it can be advantageous to administer one or more therapeutic agents to the eye, coincident with implantation of the IOL, to alleviate various side effects of the IOL or treat other conditions of the eye that might coexist with the conditions that lead to cataracts. Side-effects such as infection and inflammation, and conditions such as glaucoma, can be treated with therapeutic agents that can be incorporated into the IOL or additional devices that can be secured to the IOL. In addition to IOLs, ocular implants not including lenses can be implanted to address various such conditions.

Previous attempts have disclosed various configurations of drug delivery components to be used in conjunction with IOLs, including the placement of drug delivery components on haptics of IOLs. The devices and methods described below provide for more efficient and/or robust approaches for securing a drug delivery component to an IOL, and related drug delivery systems.

SUMMARY

In one aspect, the disclosure relates to intraocular drug delivery systems including an ocular implant and a drug delivery component, wherein the drug delivery component is non-bioerodible, and includes at least one therapeutic agent embedded within a matrix (e.g., a polymer matrix). In certain embodiments, the drug delivery component can be configured for a zero-order drug release rate, for example, for delivery over a prolonged period of time. In certain embodiments, the ocular implant can be an intraocular lens assembly.

In one embodiment of the disclosure, a stabilized intraocular drug delivery system is provided. In accordance with this embodiment, the stabilized intraocular drug delivery system includes an intraocular lens (IOL) assembly and a drug delivery component. The IOL assembly includes a lens and a haptic extending outwardly from the plane of the lens and configured to engage the drug delivery component, the IOL assembly configured for implantation into an eye of a subject. The drug delivery component includes at least one therapeutic agent, composition, and/or formulation; and a fixation portion having an opening sized and dimensioned to receive the haptic and secure the drug delivery component to the IOL assembly. In certain embodiments, the haptic includes a retention tab on the haptic, the retention tab having an outer surface and an inner surface to provide an inner portion at the junction of the haptic to the lens. The haptic further includes a gusset on a surface opposite the inner portion at the junction of the haptic to the optic/lens. In some embodiments, the fixation portion of the drug delivery component, and the retention tab, inner portion, and gusset of the haptic are configured to secure the drug delivery component to the IOL assembly in a manner that stabilizes the relative movement of the ocular implant and drug delivery component.

In certain embodiments, attachment of the drug delivery component to the intraocular lens assembly or other intraocular implant is accomplished through releasable or non-releasable means and can be accomplished at the time of manufacture of the IOL assembly, pen-operatively immediately before or after implantation, or intra-operatively, in the same procedure as the IOL assembly is implanted or post operatively.

In other embodiments, the drug delivery component can include a first and second drug delivery component and can be configured to allow for placement of the second drug delivery component into or within or surrounded by the first drug delivery component. Placement of the second drug delivery component into the first drug delivery component can be accomplished at the time of manufacture of the IOL assembly, peri-operatively immediately before or after implantation, intra-operatively, or in the same procedure as the IOL assembly is implanted. In some embodiments, the first and/or second drug delivery component can be subject to depletion, and upon depletion can be removed and replaced, in an operation that can be accomplished at any time after the surgery in which the IOL assembly is first inserted including long after the procedure is completed. In certain embodiments, the first and/or second drug delivery component can be subject to depletion, and upon depletion can be removed and replaced, in an operation that can be accomplished a few days up to several years after the surgery in which the IOL assembly is first inserted.

BRIEF DESCRIPTION OF THE DRAWINGS

FIGS. 3A and 3B illustrate top views of intraocular drug delivery systems, in accordance with embodiments of the disclosure. FIG. 3A illustrates a smaller drug delivery component attached to an IOL assembly, while FIG. 3B illustrates a larger drug delivery component attached to an IOL assembly.

FIGS. 4A-4C illustrate views of an IOL assembly, in accordance with embodiments of the disclosure. FIG. 4A illustrates a top view of an IOL assembly having an improved haptic configuration of the disclosure. FIG. 4B illustrates a bottom view of a relief cut out at a haptic-optic juncture of an IOL assembly, while FIG. 4C illustrates a cross-section view of the relief cut of FIG. 4B.

FIG. 6B illustrates an isometric view of a posterior portion of the polymer shell including the attachment structure for securing to the haptic of the IOL.

FIG. 6C illustrates an isometric view of the posterior portion of the polymer shell with the drug embedded polymer positioned within the reservoir of the polymer shell.

FIG. 6D illustrates an isometric view of the polymer shell with the drug embedded polymer positioned therein from FIG. 6C with the addition of an anterior portion of the polymer shell enclosing the drug embedded polymer therein.

DETAILED DESCRIPTION

In certain embodiments, the disclosure relates to intraocular drug delivery systems including, but not limited to, an ocular implant and a drug delivery component, wherein the drug delivery component is non-bioerodible, and includes at least one therapeutic agent releasably embedded within a matrix (e.g., a polymer matrix). In certain embodiments, the drug delivery component can be configured for a zero-order drug release rate, for example, for delivery over a prolonged period. In certain embodiments, the ocular implant can be an intraocular lens assembly.

Figure 1:
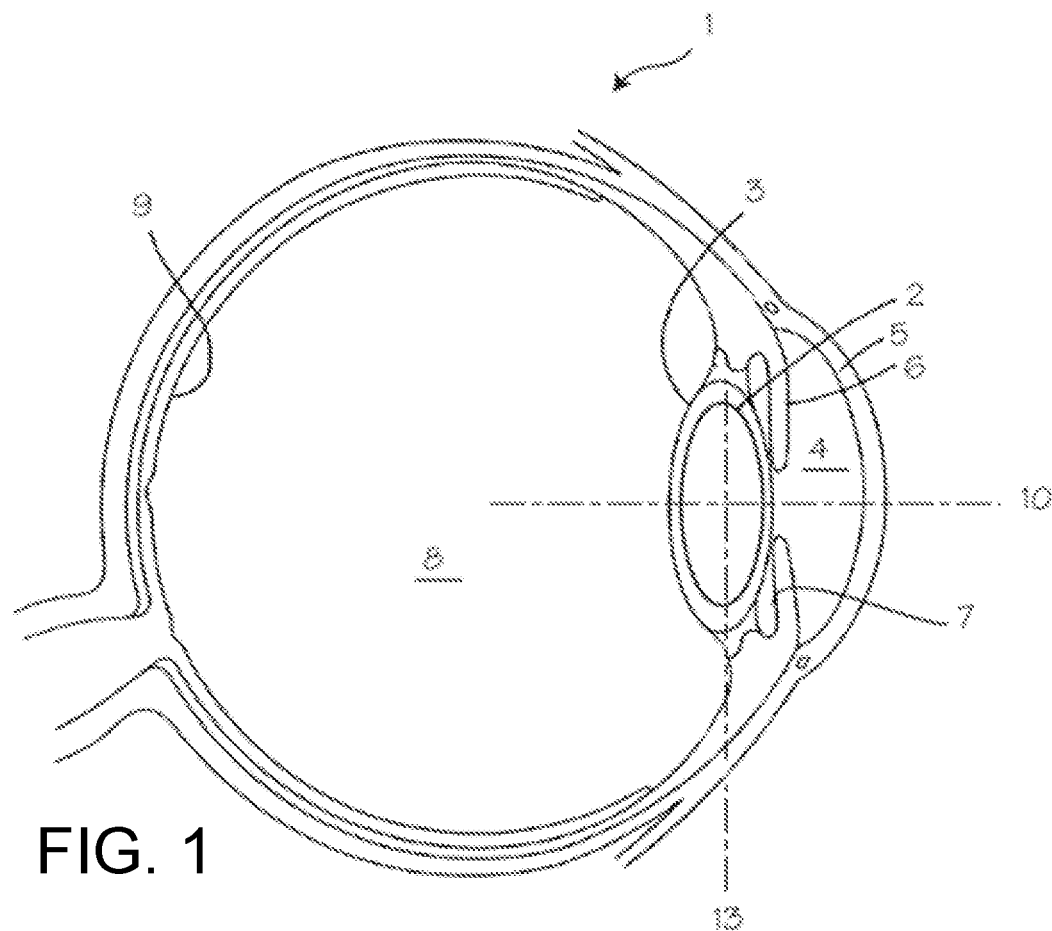
FIG. 1 and FIG. 2 illustrate an environment for use of an intraocular drug delivery system of the disclosure.
Figure 2:
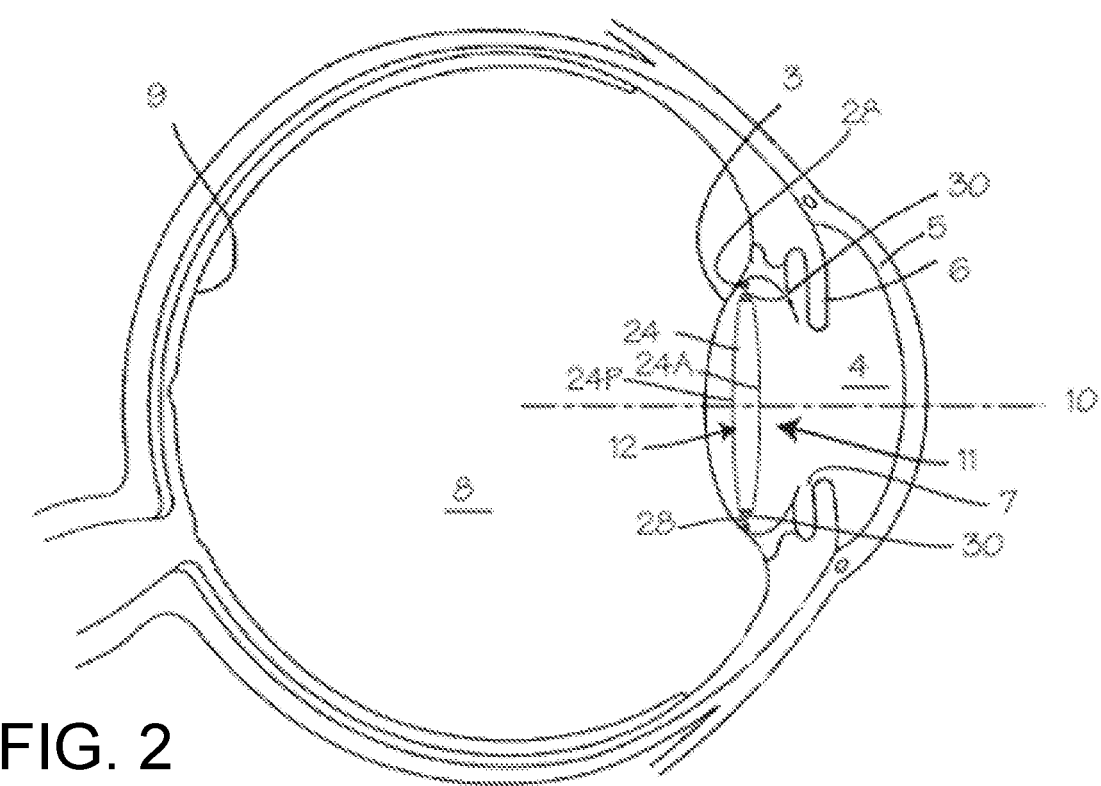

FIGS. 1 and 2 illustrate placement and use of an intraocular drug delivery system in the eye of a patient. The eye 1 includes a lens 2 (the natural lens of the eye) and lens capsular bag 3, and the anterior chamber 4 which includes the cornea 5 and iris 6 and aqueous humor filling the space between the cornea and the iris, and a posterior chamber 7 between the iris and the capsular bag. The posterior cavity/vitreous body 8 is the large space between the lens 2 and the retina 9. The natural lens 2 of the eye 1 is characterized by an optical axis 10. (In the following description of the intraocular drug delivery system, the terms posterior and anterior will be used in relation to the anatomy of the eye, in which the cornea is anterior and the retina is posterior.) FIG. 2 illustrates a placement of the intraocular drug delivery system 11 in the eye including an ocular implant 12 and drug delivery component 30, which is implanted in the capsular bag of a subject (described in more detail herein). The capsular bag can contain the native lens, an artificial lens or no lens at all.

Certain aspects of the disclosure relate to intraocular drug delivery systems including an ocular implant and a drug delivery component, where the ocular implant and the drug delivery component are connected in a configuration that stabilizes relative movement of the ocular implant and drug delivery component. In certain embodiments, the ocular implant can be an intraocular lens assembly (IOL). However, the disclosure is not so limited, and the ocular implant can serve as any suitable ophthalmic implant configured to include the drug delivery component stabilizing and retaining features described herein. The intraocular drug delivery systems can include a drug delivery component that is configured to deliver various therapeutic agents to treat various conditions and disorders of the eye.

FIGS. 3A and 3B illustrate exemplary intraocular drug delivery systems 20 which can include an IOL assembly 22 and one or more drug delivery components 30. The IOL assembly includes an annular structure 23 encircling an optic/lens 24 at the center thereof. One or more haptics 28 extend outwardly from the plane of annular structure 23 or a parallel plane. The optic/lens 24 can include an optic with vision correction. Alternatively, the annular structure 23 can simply be a scaffold to provide structural support without an optic/lens 24 positioned therein. When the IOL assembly 22 does not include an optic/lens 24, the annular structure 23 can be a complete ring (continuous perimeter), or the annular structure 23 can be a partial ring (C-shape) with ends that do not meet. The drug delivery component 30 is configured for attachment (preferably releasable attachment) to a haptic 28 of the IOL assembly 22. The intraocular drug delivery system 20 includes an anterior surface and a posterior surface, relative to the eye of subject when implanted. In other embodiments, the intraocular drug delivery system 20 can optionally include other devices such as a capsular tension ring, or a capsular scaffold for holding the system in place during use.

The outward extent of the haptic 28 is long enough to impinge on the capsular bag of the eye of subject when the system is implanted, while the radially outward extent of the drug delivery component 30, when installed on the implanted IOL assembly 22, is preferably shorter than that of the haptic 28, for example, to avoid impingement of the drug delivery component 30 on the capsular bag in the equatorial region of the capsular bag of the eye of the subject. As shown, FIG. 3A illustrates an embodiment wherein the drug delivery component 30 is configured to dimensionally correspond to the size and shape of the optic-haptic junction area, while FIG. 3B illustrates an embodiment wherein the drug delivery component 30 is configured to be dimensionally larger than the optic-haptic junction area. However, the disclosure is not so limited, and the drug delivery component 30 can be sized as shaped in any manner suitable for the intended use, e.g., one-quarter around the circumference of the optic, one-third around the circumference of the optic, one-half around the circumference of the optic, etc. In some aspects, when installed on the implanted IOL assembly 22, the drug delivery component 30 is located over the entire optic-haptic junction area or a portion or segment thereof.

In certain embodiments, the shape of the drug delivery component 30 can be a slab. In some aspects, the drug delivery component 30 can be a rectangular (e.g., square) pad or slab, or oblong configuration, or any applicable shape. In certain embodiments, the drug delivery component 30 can be a flat configuration. In some embodiments, the shape of the drug delivery component 30 can be a block, a sphere, a cylinder, or other configuration suitable to deliver the one or more therapeutic agents, compositions, and/or formulations.

The drug delivery component 30 can define a refractive index or index of refraction where this component is made up of materials having a similar refractive index. In accordance with these embodiments, drug delivery component 30 can be made up of materials causing little to no dysphotopsia to minimize or eliminate any unwanted light projections into the retina and reducing or eliminating any undesirable reflections or images (e.g., does not focus light in any intended manner). In certain embodiments, the drug delivery component 30 has a neutral refractive index or devoid of a refractive index. In some embodiments, the refractive index of the drug delivery component 30 can be about 1.1 to about 1.7. In other embodiments, the refractive index of the drug delivery component 30 can be about 1.2 to about 1.6. In certain embodiments, the refractive index of the drug delivery component 30 is about 1.3 to about 1.5. In some embodiments, the refractive index of the drug delivery component 30 is about 1.4.

FIGS. 4A, 4B, and 4C illustrate an exemplary IOL assembly 22 of the disclosure. As shown in FIG. 4A, haptic 28 is configured with retention and stabilization features including retention tab 40 and gusset 44. Retention tab 40 at a central end of haptic 28 has an outer surface and an inner surface to provide an inner portion 42 at the optic-haptic junction 48. Opposite the inner portion 42 formed by retention tab 40, the haptic 28 includes a curvilinear notch or gusset 44 that facilitates flexing and bending of the haptic during use. In some embodiments, the outer surface of the retention tab 40 includes a radial surface and the inner surface of the retention tab includes a radial surface so as to provide the inner portion of the retention tab with a curved inner portion at the junction of the haptic to the lens.

Between retention tab 40 and gusset 44, the anterior surface of haptic 28 provides an upper surface 46 which can interface with at least a portion of drug delivery component 30 to stabilize its orientation during use (see FIG. 4A). In some embodiments, upper surface 46 can be sized and shaped so as to match the size and shape of the drug delivery component 30 (e.g., interface with the entire drug delivery component 30 or substantially the entire drug delivery component 30). As illustrated in FIG. 4B, in some embodiments, the portion 81 connecting the haptic 28 to the optic body 82 is formed with a contoured relief cut 84, which provides additional stability to the drug delivery component during use and/or to maintain a PCO barrier. FIG. 4C illustrates a detailed view of relief cut 84 and surface 46 of haptic 28.

Figure 5:
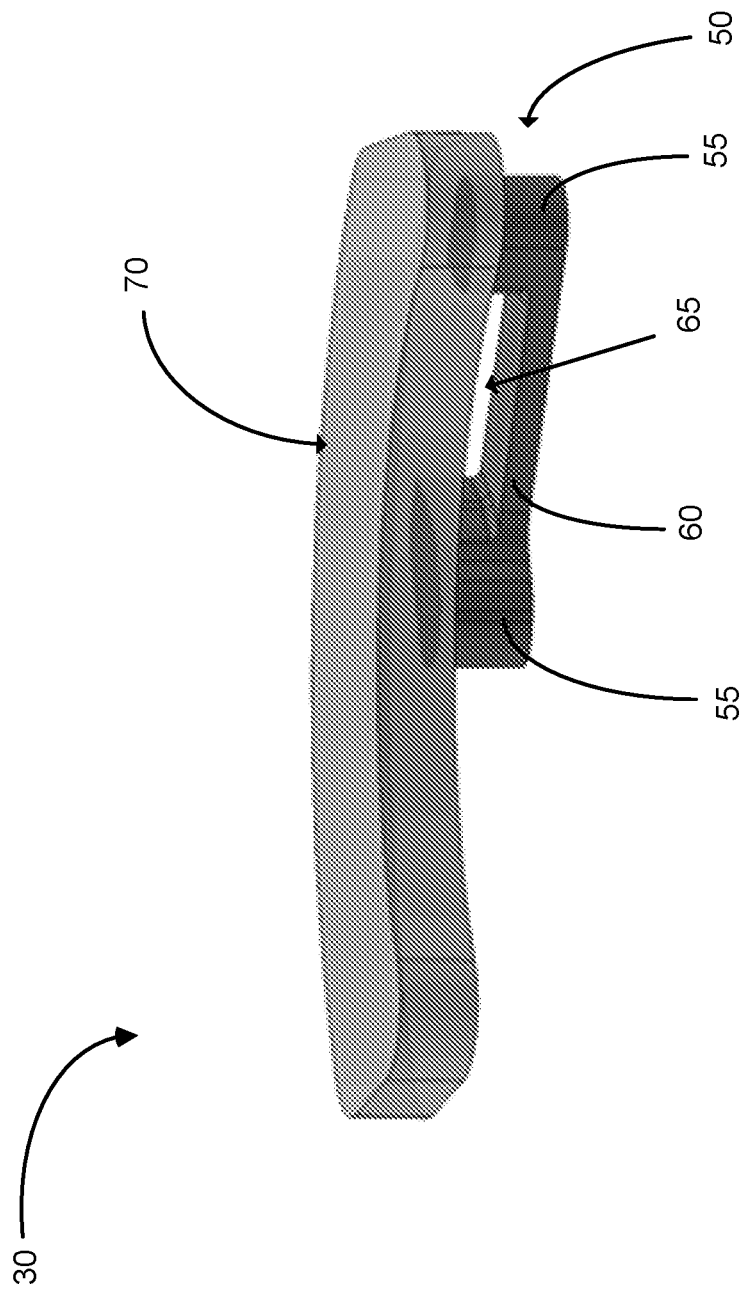
FIG. 5 illustrates an isometric view of a drug delivery device, in accordance with embodiments of the disclosure.

FIG. 5 illustrates an exemplary drug delivery component 30 of the disclosure. The drug delivery component 30 can include at least one therapeutic agent, formulation, or pharmaceutical composition, which can occupy the entirety of drug delivery pad 70, be uniformly distributed thereof or occupy a portion thereof (such as an interior drug delivery pad, gel, or drug eluting matrix). The drug delivery pad 70 can elute the at least one therapeutic agent, formulation or composition. In certain embodiments, the drug component 100 (also referred to as a drug core or a polymer core, in certain embodiments) can be dissolvable, bioerodible, and/or biodegradable over time. In some embodiments, the drug component 100 is a solid. In some embodiments, the drug component 100 is a liquid composition including at least one therapeutic agent. In other embodiments, the drug delivery pad 70 is not dissolvable, bioerodible, or biodegradable over time. In accordance with these embodiments, the at least one therapeutic agent, formulation or composition can be eluted from the drug delivery pad 70 and the drug delivery pad 70 maintains its configuration throughout the elution process without dissolving, degrading and/or eroding. In certain embodiments, the at least one therapeutic agent (e.g., bimatoprost) can include an amorphous solid, a crystalline, microparticle, microbead, spray-dried compound or agent, lyophilized pharmaceutical agents, or other suitable form, or a combination thereof. In certain embodiments, the at least one therapeutic agent includes a crystalline form, amorphous form, mixture of crystalline form and amorphous form of the at least one therapeutic agent, or other dry form of the at least one therapeutic agent including, but not limited to, a conjugated form or salt form thereof, or other derivative form thereof of the at least one therapeutic agent. In some embodiments, the at least one therapeutic agent can include a range of about 30% crystalline to about 70% crystalline form or about 40% to about 60% crystalline form. In other embodiments, the at least one therapeutic agent can include a range of 0% to about 20% crystalline form (e.g., 0% crystalline is where the at least one therapeutic agent is amorphous). Drug delivery component 30 can further include an attachment structure or fixation portion 50 affixed to the posterior side of the drug delivery pad 70. Attachment structure 50 can include structures 55 which extend vertically from the posterior side of drug delivery pad 70 and are connected by a horizontally extending band 60 to form an opening 65, (e.g., a slot, aperture, or compartment). The opening 65 is configured to receive the haptic of an IOL assembly, such that the haptic (not shown) can pass through the opening 65. The attachment structure 50 can generally function as a drug delivery component retention loop, and can be formed or made from any suitable materials for the intended use. By way of non-limiting example, the fixation portion 50 can be formed from biocompatible polymers for ophthalmic use that are compatible with the intended therapeutic agents, e.g., medical grade silicone or similar material. Further, the fixation portion 50 can be attached to the drug delivery pad 70 by any method known in the art suitable for such purposes, e.g., co-molded medical grade adhesives, thermal bonding, etc. Further features of the drug delivery component or drug dispenser 30 are described in U.S. Patent Application No. 63/226,507, filed Jul. 28, 2021, which is incorporated by reference herein in its entirety.

The retention and stabilization features of the ocular implant and the fixation portion of the drug delivery component provide intraocular drug delivery systems in a configuration that stabilizes relative movement of the ocular implant and drug delivery component.

Figure 6A:
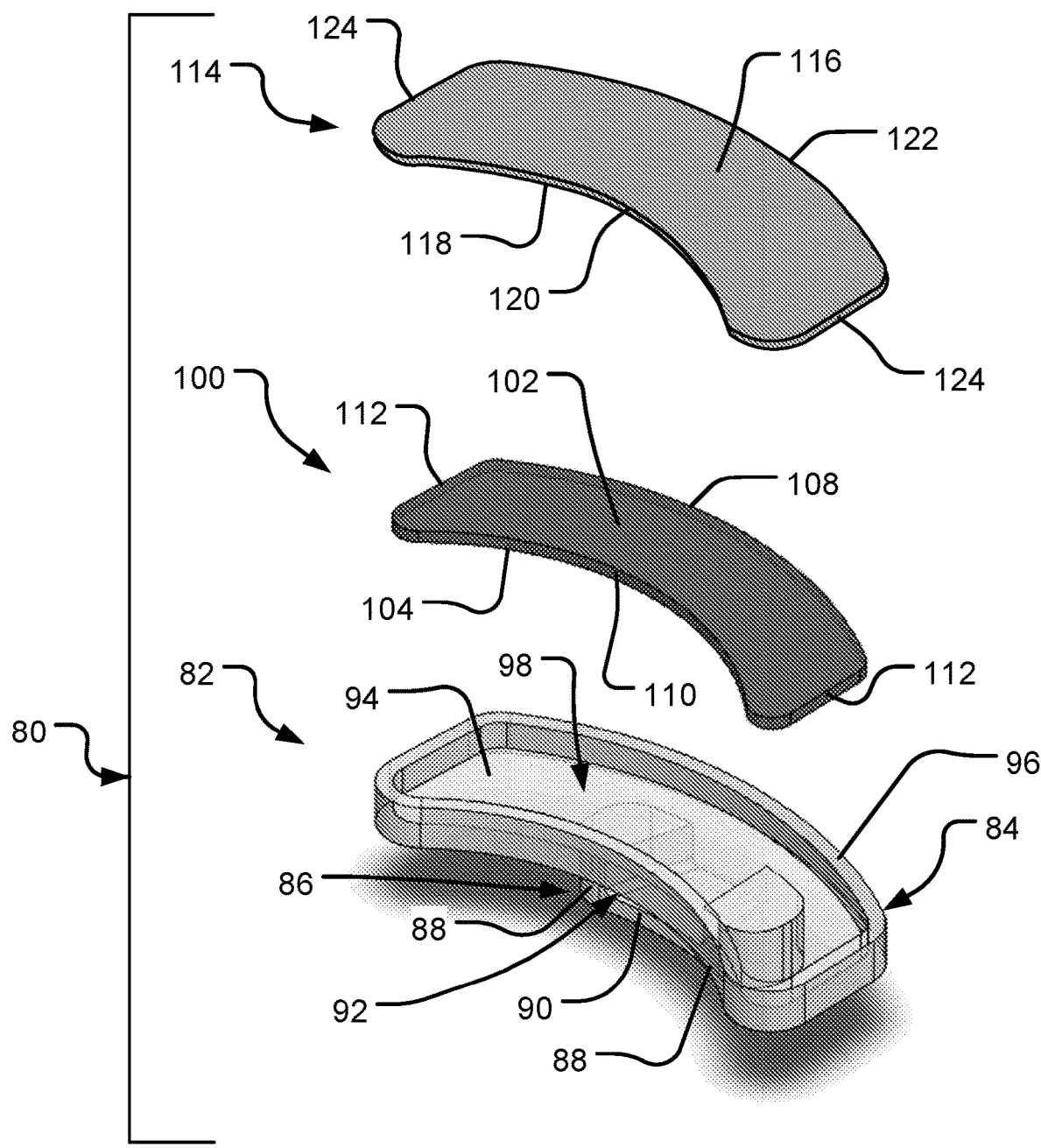
FIG. 6A illustrates an exploded isometric view of the drug delivery device of FIG. 5.

FIGS. 6A-6D illustrate various views of an exemplary drug delivery component 80. More particularly, FIG. 6A illustrates an exploded isometric view of the drug delivery component 80, which includes many of the same features of the drug delivery component 30 of FIG. 5. As illustrated in FIG. 6A, the drug delivery component 80 includes a base structure 82 including a tray 84 and an attachment structure 86 extending from a posterior side of the tray 84. The attachment structure 86 facilitates coupling the drug delivery component 80 to the haptic (not shown) of an intraocular implant. The attachment structure 86 of FIG. 6A can include the same or similar features as the attachment structure 50 of FIG. 5. Still referring to FIG. 6A, the attachment structure 86 includes a pair of posts 88 extending from the posterior side of the tray 84. The pair of posts 88 is connected with a band 90. Together with the posterior side of the tray 84, the pair of posts 88, and the band 90, an aperture 92 is formed for receiving the haptic of the intraocular implant there through.

The tray 84 of the base structure 82 includes a base surface 94 and an outer rim 96 that extends along the edge of the base surface 94. Together with the base surface 94 and the rim 96, the tray 84 forms a reservoir, trough, or recess 98 for receiving a drug component 100, which is illustrated in FIG. 6A. In certain embodiments, the base structure 82 can be formed of the same or similar material as the encapsulation sheet 114 (which is discussed below). For example, the base structure 82 can be formed of a non-bioerodible, non-biodegradable material (e.g., a polymer or the like). In certain embodiments, the polymer can be a crosslinked polymer. In other embodiments, the polymer can be a mixed polymer. In some embodiments, the crosslinked polymer can have a molecular weight cutoff of about 5,000 to about 250,000 molecular weight (mw); or about 5,000 to about 200,000 mw. In certain embodiments, the base structure 82 can be formed of a biocompatible polymer such as silicone or silicone composite material or a mixture of silicones. In certain embodiments, the biocompatible, non-bioerodible polymer can be formed by curing a two-part liquid silicone rubber mixture. In certain embodiments, the two-part liquid silicone rubber mixture can be formed by a predetermined ratio of the two-part liquid silicone. In some embodiments, 2-part silicone mixtures are well known in the art and any pharmaceutically acceptable silicone mixture is contemplated of use herein; for example, to encase or secure the at least one therapeutic agent for delivery over a prolonged period. For example, a two-part liquid silicone rubber mixture can include x and y at a ratio of about 50:50, 55:45, 45:55, 40:60, 60:40. In another example, the ratio of x and y can be about 10:1. In the case of the base structure 82 being silicone or a mixture of silicone or a two-part liquid silicone rubber mixture with or without other non-bioerodible, biocompatible material, the base structure 82 is non-bioerodible and/or non-biodegradable. That is, the base structure 82 does not erode when positioned in the eye, does not dissolve when positioned in the eye and is non-absorbable within the eye after placement. Stated differently, the base structure 82, when formed of a non-bioerodible, non-biodegradable material such as silicone and the like, will retain its shape and structure in the eye and not erode or degrade over time. Materials that erode or degrade in the eye can pose challenges with clarity of vision, irritation within the eye (e.g., iritis), cause infections in the eye, and injure cells resulting in cell death within the eye or other side effects which can lead to permanent damage to the eye. In certain embodiments, the base structure 82 can be manufactured from a non-bioerodible and/or non-biodegradable material. By way of non-limiting example, the base structure 82 can be manufactured from at least one material, including, but not limited to, any inorganic non-bioerodible and/or non-biodegradable synthetic polymer (e.g., silicone, polysiloxane, or a mixture of two or more silicone materials or the like), poly olefins (e.g. polyethylene), polymethacrylate, polystyrene, poly(vinyl acetate), polyurethane and/or polytetrafluoroethylene. In other embodiments, co-polymers or a mixture of polymers can be used of these and similar agents, for example, ethylene vinyl acetate and the like. In other embodiments, the base structure 82 can be manufactured from a molding process such as injection molding or cast molding or other molding process known in the art. In still other embodiments, the base structure 82 can be manufactured by an extrusion process or the like.

As illustrated in FIG. 6A, the drug component 100 (also referred to as a drug core or a polymer core, in certain embodiments) is sized and shaped to be received within the reservoir 98 of the base structure 82 of the drug delivery component 80. That is, the shape the drug component 100 is matching to the reservoir 98 so as to be matingly received within the reservoir 98. The drug component 100 includes generally planar top and bottom surfaces 102, 104 and an edge between the top and bottom surfaces 102, 104 that includes a convex edge surface 108, a concave edge surface 110 the convex edge surface 108, and a pair of linear edge surfaces 112 that are opposite each other and generally parallel with each other. The drug component 100 generally forms an arcuate pad in shape.

The drug component 100 can include at least one active agent such as at least one therapeutic agent, formulation or composition embedded within a biocompatible polymer matrix. The drug component 100 may be referred to as a drug core, or a polymer core when the at least one active agent is embedded within a polymer matrix. In accordance with these embodiments, the active agent, formulation, and/or composition can be mixed with a polymer (or mixture of polymers) and formed into the arcuate pad shape or other appropriate shape as illustrated in in FIG. 6A. Once mixed, this combination of the active agent, formulation, or composition can be essentially uniformly dispersed and/or embedded within the polymer matrix (or mixture of polymers). In accordance with these aspects, the active agent, formulation, and/or composition can be embedded within a polymer matrix making up the drug component 100. The polymer matrix with the embedded active agent, formulation and/or composition can be dispensed into a mold for curing to create a drug component 100. The drug component 100 is a drug eluting component that is configured to deliver a consistent or steady-state release of the active agent, formulation and/or composition from within the polymer matrix. The polymer mixed with the active agent, formulation or composition can be a biocompatible, non-bioerodible polymer such as silicone or other polymer or mixture of polymers disclosed herein. In certain embodiments, biocompatible, non-bioerodible polymer (e.g., silicone) can be the same type of biocompatible, non-bioerodible polymer that is used to form the base structure 82.

In other aspects, the drug component 100 delivers a zero-order release of the at least one therapeutic agent, which is further illustrated and described with reference to FIGS. 8 and 9. As described herein, a zero-order release (or elution) means the at least one therapeutic agent, formulation and/or composition is released at or about or essentially at a constant rate over a prolonged period of time (e.g., years). In certain embodiments, zero-order release means that the at least one therapeutic agent, formulation and/or composition is released at or about at a steady-state rate (e.g., essentially steady-state release) for prolonged period. In some examples, the period of time of zero-order release of the at least one therapeutic agent, formulation and/or composition is about 3 months up to about 10 years or any period in between. In other embodiments, the period of time of zero-order release of the at least one therapeutic agent, formulation and/or composition is about 6 months to about 6 years or any time in between. In some examples, the period of time of zero-order release of the at least one therapeutic agent, formulation and/or composition is about 9 months to about 3 years or any time in between. In some embodiments, the period of time of zero-order release is about a year to about 6 years or any time in between.

In certain embodiments and as previously described (with reference to FIG. 6A), the drug component 100 can be formed of the same or similar material as the base structure 82 and/or the encapsulation sheet 114. For example, the drug component 100 can be formed of a non-bioerodible, non-biodegradable polymer or mixture of polymers. In certain embodiments, the drug component 100 includes one or more dried pharmaceutical agents intermixed therein (e.g., intermixed within the polymer core). In some aspects, the one or more pharmaceutical agents can be soluble when encapsulated by a membrane, such as when it is within the base structure 82 and the encapsulation sheet 114. In certain embodiments, the one or more therapeutic agents can be dried when encased in a core disclosed herein. In other embodiments, the one or more therapeutic agents can be melted and mixed for encasing in a core. In some aspects, the drug component 100 is non-refillable. In other embodiments, the one or more pharmaceutical agents can be uniformly or essentially uniformly distributed through non-bioerodible, non-biodegradable polymer or mixture of polymers forming the drug component 100. In accordance with these embodiments, the one or more pharmaceutical agents can be delivered to a subject at an essentially steady state rate for a pre-determined period of time (e.g., 1 month up to about 10 years).

In certain embodiments, the drug component to be embedded within the polymer matrix can include one or more therapeutic agents, formulation, and/or composition of use to treat, ameliorate, prevent, and/or reduce the risk of onset of a condition or disorder of the eye. In certain embodiments, the drug delivery component 80 includes about 1 mg up to about 1000 mgs; or about 10 mg up to about 750 mgs; or about 50 mg up to about 500 mgs of the one or more therapeutic agent, formulation, and/or composition. In certain embodiments, two drug delivery components 80 can include about 2 mgs up to about 2,000 mgs of the one or more therapeutic agent, formulation, or composition. In certain embodiments, the drug component to be embedded within the polymer matrix can include one or more therapeutic agents, formulation, and/or composition without preservative, for example preservative free. In some embodiments, the at least one therapeutic agent to be included for example in a core can include, but is not limited to, bimatoprost. In accordance with these embodiments, the bimatoprost can by between 1.0% to about 25.0% w/w. In other embodiments, the at least one therapeutic agent can be as high as about 40% w/w, or about 50% w/w, or about 60% w/w depending on the at least one therapeutic agent being used, and the polymer matrix being formed. In certain embodiments, one of skill in the art would understand that the polymer matrix must be able to cure in the presence of the one or more therapeutic agent.

In some embodiments, the drug delivery component 80, and more particularly, the polymer matrix and the at least one therapeutic agent, formulation, and/or composition of the drug component 100 forming a polymer core can include the following weight ratios. In certain embodiments, the weight ratio of the at least one therapeutic agent and the biocompatible, non-bioerodible polymer matrix can be a predetermined ratio of about 100:1 (w/w) to about 1:100; or about 60:1 or 1:60, or about 50:1 to about 1:50; or about 40:1 or 1:40, or about or about 20:1 to about 1:20; or about 10:1 to about 1:10; or about 5:1 to about 1:5; or about 3:1 to about 1:3 or any ratio in between these ratios, or other predetermined ratio of polymer matrix to at least one therapeutic agent appropriate for the treatment time period of delivery to a subject's eye to be covered (e.g. 1 month up to about 10 years). In certain embodiments, the weight ratio of the at least one therapeutic agent to the biocompatible polymer matrix can be about 1:3 or about 2:3. In certain embodiments, a concentration of the at least one therapeutic agent, formulation and/or composition of a core region harboring the at least one therapeutic agent, formulation and or composition can be at least about 0.2% w/v up to about 40% w/v. In other embodiments, a concentration of the at least one therapeutic agent, formulation and/or composition of a core region harboring the therapeutic agent can be at least about 0.4% w/w up to about 40% w/w. In certain embodiments, a concentration of the at least one therapeutic agent, formulation and or composition of a core region harboring the at least one therapeutic agent, formulation and/or composition can be about 10% to about 40% w/v.

In certain embodiments, at least one therapeutic agent, formulation, and/or composition (e.g., bimatoprost) has a pre-determined liquid content or water content. In some embodiments, the water content of the at least one therapeutic agent, formulation, and/or composition is 5% or less. In some aspects, the water content of the at least one therapeutic agent, formulation, and/or composition is 4% or less. In other embodiments, the water content of the at least one therapeutic agent, formulation, and/or composition is 3% or less. In certain embodiments, the water content of the at least one therapeutic agent, formulation, and/or composition is 2% or less. In some embodiments, the water content of the at least one therapeutic agent, formulation, and/or composition is 1% or less.

In certain embodiments, an average particle size of the at least one therapeutic agent, formulation, and/or composition to be mixed with a biocompatible, non-bioerodible polymer disclosed herein can be 50 µm or less. In some embodiments, an average particle size of the at least one therapeutic agent, formulation, and/or composition disclosed herein 45 µm or less. In some embodiments, an average particle size of the at least one therapeutic agent, formulation, and/or composition disclosed herein 40 µm or less. In certain embodiments, an average particle size of the at least one therapeutic agent, formulation, and/or composition disclosed herein 35 µm or less. In some aspects, an average particle size of the at least one therapeutic agent, formulation, and/or composition disclosed herein 30 µm or less. In other embodiments, an average particle size of the at least one therapeutic agent, formulation, and/or composition disclosed herein 25 µm or less. In some aspects, an average particle size of the at least one therapeutic agent, formulation, and/or composition disclosed herein 20 µm or less. In other embodiments, an average particle size of the at least one therapeutic agent, formulation, and/or composition disclosed herein 15 µm or less. In some embodiments, an average particle size of the at least one therapeutic agent, formulation, and/or composition disclosed herein 10 µm or less. In certain embodiments, an average particle size of the at least one therapeutic agent, formulation, and/or composition or essentially dried at least one therapeutic agent, formulation and/or composition disclosed herein 5 µm or less. In some embodiments, the at least one therapeutic agent disclosed herein can be melted into the biocompatible, non-bioerodible matrix where particle size is irrelevant. In other embodiments, a drug delivery device can include a core of varying size to accommodate the at least one therapeutic agent when needed to suitably house or embed the at least one therapeutic agent, for example, by increasing the size of the core being used relative to the particle size of the at least one therapeutic agent of interest.

In some embodiments and further to the preceding paragraphs, the at least one therapeutic agent, formulation, and/or composition of use in devices disclosed herein can be used for the treatment, prevention, or amelioration of a condition of the eye. In accordance with these embodiments, eye conditions targeted by devices and methods disclosed herein include, but are not limited to, glaucoma. cataract inflammation, chronic uveitis, age-related macular degeneration (AMD), macular degeneration, ocular hypertension, inflammation, edema, eye infections, or combinations thereof, or other eye conditions thereof. In certain embodiments, the at least one therapeutic agent, formulation, and/or composition of use in devices disclosed herein can be used for the treatment, prevention, or amelioration of a condition of the eye requiring long-term treatment such as a month, several months to years of treatment. In other embodiments, the at least one therapeutic agent, formulation, and/or composition of use in devices disclosed herein can be used to treat, regulate, reduce, or inhibit symptoms of, or otherwise benefit ophthalmic or systemic diseases or conditions in a subject in need thereof. In accordance with these embodiments, the at least one therapeutic agent, formulation, and/or composition embedded or encased in a drug delivery component disclosed herein can include, but is not limited to, bimatoprost, brimonidine, latanoprost, timolol, pilocarpine, brinzolamide and other agents identified as beta blockers, alpha agonists, rho kinase inhibitors such as rho-associated protein kinase inhibitor or ROCK inhibitor (e.g., ROCK1 (ROKβ) and ROCK2 (ROKα)), tyrosine kinase inhibitors (TKIs) (e.g., carnosol and ursolic acid, imatinib, gefitinib, erlotinib, sorafenib, sunitinib, and dasatinib), rho kinase inhibitors, adenosine receptor agonists, carbonic anhydrase inhibitors, adrenergic and cholinergic receptor activating agents, prostaglandin analogues, and similar agents thereof and any combination thereof. In certain embodiments, the at least one therapeutic agent, formulation, and/or composition of use to treat the eye condition (e.g., glaucoma) can be a liquid or can be in an essentially dry or dehydrated or lyophilized form or in a crystalline form. In certain embodiments, the at least one therapeutic agent, formulation, and/or composition embedded or encased in a drug delivery component disclosed herein includes, but is not limited to, bimatoprost, brimonidine, and/or latanoprost in a liquid, dehydrated, lyophilized or crystalline form.

In other embodiments and further to the previous paragraphs, the at least one therapeutic agent, formulation, and/or composition of use in devices disclosed herein can be used in the treatment, prevention, or amelioration of wet macular degeneration. In accordance with these embodiments, the at least one therapeutic agent, formulation, and/or composition can include, but is not limited to, aflibercept, bevacizumab, pegaptanib, ranibizumab, or other agent for treating wet macular degeneration, a steroid, one or more aptamers, and combinations thereof.

In yet other embodiments and as previously described, the therapeutic agent can be used in the treatment, prevention, or amelioration of dry macular degeneration. In accordance with these embodiments, the therapeutic agent, formulation, or composition of use in devices disclosed herein can include, but is not limited to, one or more complement factors, anti-oxidants, anti-inflammatory agents, or other appropriate agent for treating or preventing dry macular degeneration, and combinations thereof.

In other embodiments and as previously described, the at least one therapeutic agent, formulation, and/or composition can be used in the treatment, prevention, or amelioration of uveitis. In accordance with these embodiments, the at least one therapeutic agent, formulation, and/or composition can include, but is not limited to, methotrexate or similar agent (e.g., to attack DNA in a specific cell population and reduce cell growth within the eye of a subject), antibodies directed to treat uveitis, dexamethasone, triamcinolone, other steroid agents appropriate to treat uveitis, or any combination thereof. In other embodiments, the at least one therapeutic agent can also include, but are not limited to, anti-proliferative agents, anti-mitotic agents, anti-inflammatory agents, and other pharmaceutical agents or formulations that can reduce or inhibit the expansion of lens epithelial cells, e.g., to treat posterior capsular opacification.

In yet other embodiments and as previously described, antibiotics, or other anti-microbial agents, such as fluoroquinolones, non-steroidal agents such as ketorolacs, and steroids such as prednisolones can be incorporated into a drug delivery component disclosed herein for post-op management after eye surgery such as cataract, glaucoma, or other eye surgery. In accordance with these embodiments, these implants can be used in order to improve outcome and reduce complications of the eye post procedure.

In certain embodiments and as previously described, the at least one therapeutic agent or active agent can include, but is not limited to, one or more of a protein, polypeptide, polynucleotide, carbohydrate, fatty acid, a small molecule, and an aptamer of use to treat, prevent or ameliorate a disorder in the eye of a subject. In certain embodiments, the at least one therapeutic agent or active agent includes one or more of a beta blocker, alpha agonists, an antibiotic, a chemotherapeutic agent (e.g., to reduce complications of excess cell proliferation), a prostaglandin analog, rho kinase inhibitors such as rho-associated protein kinase inhibitor or ROCK inhibitor, a tyrosine kinase inhibitor (TKI), a carbonic anhydrase inhibitor, a steroid, glucocorticoid, NSAIDs, anti-fibrotic agent, an anti-oxidant, an anti-mitotic agent, a miotic agent, a mydriatic agent, an anti-neoplastic agent, a 11β-Prostaglandin F2α or a 11-epi-PGF2α agent, an antibody directed to treat an eye disorder, other agent that lowers intraocular pressure, an agent that promotes nerve regeneration, an anti-inflammatory agents, an anti-autoimmune agent or a combination thereof. In certain embodiments, the at least one therapeutic or active agent can include, but is not limited to, one or more of travoprost, latanoprost, tafluprost, timolol, bimatoprost, brimonidine, brinzolamide, aflibercept, bevacizumab, pilocarpine, ethacrynic acid, CNP/BNP/ANP, tetrahydrocannabinol (THC), pegaptanib, ranibizumab, methotrexate, dexamethasone, triamcinolone, ketorolac, dorzolamide, prednisolone, cannabidiol (CBD), cannabinoids or other molecule derived from a *cannabis* plant, or a combination thereof and/or other agents used to treat glaucoma, macular degeneration, or other ocular condition for a short or prolonged period. In certain embodiments, the at least one therapeutic agent or active agent can include, but is not limited to, bimatoprost and/or dexamethasone. In certain embodiments, the bimatoprost can include, but is not limited to, bimatoprost form A. In certain embodiments, the at least one therapeutic agent, formulation and/or composition includes bimatoprost in the form of bimatoprost form A. In some embodiments, the bimatoprost agent of use herein can include a composition of bimatoprost including, but not limited to, bimatoprost form A, or other bimatoprost forms, as well as a derivative or modified form of bimatoprost thereof (e.g., 15-epi Bimatoprost, 5,6-trans bimatoprost).

In certain embodiments and as previously described, at least one therapeutic or active agent or formulation or combination thereof includes, but is not limited to, bimatoprost, brimonidine, latanoprost, timolol, pilocarpine, brinzolamide, Aflibercept, bevacizumab, pegaptanib, ranibizumab, methotrexate, dexamethasone, triamcinolone, ketorolac, dorzolamide and/or prednisolone or similar therapeutic agent or any agent capable of treating an eye condition, or any agent capable of treating any eye condition for prolonged period. In other embodiments, any therapeutic agent, composition, or formulation of use to treat the eye capable of being embedded in, and delivered from a non-bioerodible polymer is contemplated of use in drug delivery devices disclosed herein (e.g., embedded in a core). In accordance with these embodiments, the at least one therapeutic agent or active agent, formulation or composition, or combination thereof can be introduced to or provided to or be part of a drug delivery component of use in devices contemplated herein and as disclosed herein.

Still referring to FIG. 6A, the drug delivery component 80 can include an encapsulation sheet 114 that is sized and shaped to be sealed to or to seal the rim 96 of the base structure 82 in order to encapsulate or encase the drug component 100 within the reservoir 98. The encapsulation sheet 114 includes a top surface 116 (anterior surface), a bottom surface 118 opposite the top surface 116, and a side edge extending between the top and bottom surfaces 116, 118. The side edge includes a concave edge surface 120, a convex edge surface 122, and a pair of linear side edges 124 on opposite ends of the encapsulation sheet 114. In certain embodiments, the encapsulation sheet 114 can be formed of the same or similar material as the base structure 82. For example, the encapsulation sheet 114 can be formed of a non-bioerodible, non-biodegradable polymer. In certain embodiments, the encapsulation sheet 114 can be formed of a non-bioerodible, non-biodegradable, biocompatible polymer such as silicone or similar polymer. In other embodiments, when the polymer is silicone, the silicone can be the same type of silicone used to form the base structure 82, and/or the same type of silicone used to form the biocompatible polymer matrix which embeds the at least one therapeutic or active agent(s), composition and/or formulation thereof. In certain embodiments, the encapsulation sheet 114 can be formed by applying one or more layers of the biocompatible polymer over the drug component 100 positioned within the reservoir 98 of the base structure 82. The one or more layers of the biocompatible polymer can be secured to the rim 96 of the base structure 82 to encapsulate or enclose or more securely encase the drug-containing component 100 therein.

In certain embodiments, the base structure 82 and the encapsulation sheet 114 can be formed of the same or similar material. For example, the encapsulation sheet 114 can be formed of a non-bioerodible, non-biodegradable polymer. Together, the encapsulation sheet 114 and the base structure 82 can form a non-bioerodible, non-biodegradable polymer membrane that surrounds or encapsulates the drug component 100. In this manner, the polymer membrane formed by the encapsulation sheet 114 and the base structure 82 can form a matrix to elute the one or more pharmaceutical agents from the drug component 100. In certain embodiments, the polymer membrane is devoid of holes (e.g., mechanical fenestrations).

FIGS. 6B-6D illustrate various steps or in the manufacturing process of the drug delivery component 80. FIG. 6B illustrates an isometric view of the base structure 82 without the drug-containing component 100 or the encapsulation sheet 114. FIG. 6C illustrates an isometric view of the base structure 82 with the drug component 100 positioned within the reservoir 98 of the tray 84 of the base structure 82. As illustrated in this figure, the shape of the drug-containing component 100 mimics the shape of the reservoir interior or reservoir 98. That is, the generally planar bottom surface (not shown) of the drug-containing component 100 abuts the generally planar surface 94 of the tray 84 of the base structure 82. In certain embodiments, the generally planar top surface 102 of the drug-containing component 100 is exposed for encapsulation or encasement.

FIG. 6D illustrates an isometric view of the base structure 82 with the drug-containing component 100 positioned therein and with the addition of the encapsulation sheet 114 enclosing the drug-containing component 100 therein. As illustrated in the figure, the encapsulation sheet 114 is secured to the rim 96 of the base structure 82. Applying the encapsulation sheet 114 can be performed by applying one or more layers of biocompatible polymer such as silicone to the assembly of the base structure 82 and drug-containing component 100 of FIG. 6C. Alternatively, the encapsulation sheet 114 can be formed separately into the sheet illustrated in FIG. 6A and adhered to the rim 96 of the base structure 82 with an adhesive (e.g., silicone or other suitable adhesive).

In an assembled state of the drug delivery component 80, as illustrated in FIG. 6D, the drug-containing component 100 is designed to elute or allow to be released therefrom, the at least one therapeutic agent, formulation and/or composition through the polymer matrix and through the polymer encasement or polymer shell formed by the encapsulation sheet 114 and the base structure 82. In certain embodiments, the biocompatible polymer coating can have a thickness of about 25 percent up to about 300 percent of a thickness of the biocompatible polymer matrix with the at least one therapeutic agent, formulation and/or composition embedded therein. In certain embodiments, the biocompatible polymer coating can have a thickness of about 50 percent up to about 200 percent of a thickness of the biocompatible polymer matrix with the at least one therapeutic agent, formulation and/or composition embedded therein. In certain embodiments, the biocompatible polymer coating can have a thickness of about 100 percent to about 300 percent of a thickness of the biocompatible polymer matrix with the t at least one therapeutic agent, formulation and/or composition embedded therein.

In certain embodiments, a drug pad (e.g., the drug component 100) is a diffusion control system. For example, the drug component 100 can provide rate limiting diffusion of the at least one therapeutic agent, formulation and/or composition therein. In certain embodiments, an encapsulation layer (e.g., base structure 82, encapsulation sheet 114) is a controlling membrane or diffusion control. For example, the base structure 82 and/or encapsulation sheet 114 can control the rate of elution of the at least one therapeutic agent, formulation and/or composition. In some embodiments, the rate of elution is a generally constant release rate (e.g., a daily release rate or predetermined release rate). In certain embodiments, the capsular bag of the eye of the subject is a microporous membrane providing additional features for delivering the at least one therapeutic agent, formulation and/or composition to the eye of a subject. For example, the capsular bag can provide biological or naturally-occurring rate limiting diffusion. In some embodiments, as the at least one therapeutic agent, formulation and/or composition elutes (or diffuses), the at least one therapeutic agent, formulation and/or composition is delivered to the aqueous humor.

In some embodiments, the silicone membrane (e.g., encapsulation sheet 114) surrounding or covering the drug delivery component 80 can have a thickness of about 1.0 microns to about 3.0 millimeter. In certain embodiments, the silicone membrane (e.g., encapsulation sheet 114) surrounding or covering the drug delivery component 80 has a thickness of about 5.0 microns to about 2.0 millimeter. In certain embodiments, the silicone membrane (e.g., encapsulation sheet 114) surrounding or covering the drug delivery component 80 has a thickness of about 10.0 microns to about 2.0 millimeter. In certain embodiments, the silicone membrane (e.g., encapsulation sheet 114) surrounding or covering the drug delivery component 80 has a thickness of about 15.0 microns to about 2.0 millimeter. In certain embodiments, the silicone membrane (e.g., encapsulation sheet 114) surrounding or covering the drug delivery component 80 has a thickness of about 2.0 millimeter. In certain embodiments, the silicone membrane (e.g., encapsulation sheet 114) surrounding or covering the drug delivery component 80 has a thickness of about 1.0 millimeter. In certain embodiments, the silicone membrane (e.g., encapsulation sheet 114) surrounding or covering the drug delivery component 80 has a thickness of about 15.0 microns. In certain embodiments, the silicone membrane (e.g., encapsulation sheet 114) surrounding or covering the drug delivery component 80 has a thickness of about 10.0 microns. In certain embodiments, the silicone membrane (e.g., encapsulation sheet 114) surrounding or covering the drug delivery component 80 has a thickness of about 5.0 microns. In certain embodiments, the silicone membrane (e.g., encapsulation sheet 114) surrounding the drug delivery component 80 has a thickness of about 1.0 microns.

In certain embodiments, the polymer encasement is non-bioerodible, non-biodegradable. In accordance with these embodiments, the polymer encasement remains intact and without degradation or deterioration. In certain embodiments, the biocompatible polymer is hydrophilic. In other embodiments, the biocompatible polymer is hydrophobic. In accordance with these embodiments, dose and duration of elution can be influenced by the concentration of the at least one therapeutic agent, composition and/or formulation in drug-containing component 100 and/or the surface area of drug-containing component 100. Accordingly, there can be different sized drug delivery components 80, such as those illustrated in FIGS. 3A and 3B, which can be selectively implanted to provide a desired dose and duration of the at least one therapeutic or active agent, formulation or composition, or combination of agents thereof.

In some embodiments, the drug delivery component 100 can include surface areas of varying sizes. In certain embodiments, the anterior surface of the drug delivery component 80 can be about 0.1 mm² to about 20.0 mm² or about 0.3 mm² to about 15.0 mm² or about 0.5 mm² to about 12.0 mm². In certain embodiments, the posterior (i.e., bottom) surface area of the pad can be about 0.1 mm² to about 20.0 mm² or about 0.3 mm² to about 15.0 mm² or about 0.5 mm² to about 12.0 mm². In some embodiments, the surface area of the perimeter of the pad can be about 1.5 mm² to about 10 mm². In other embodiments, the total surface area of the drug delivery component 80 can be about 18.0 mm² to about 100.0 mm². In yet other embodiments, the total volume of an upper pad can be about 1.5 mm³ to about 8.0 mm³ or about 3.0 to about 5.0 mm³ or about In certain embodiments, total surface area of a drug delivery component disclosed herein is not the sum of the top, bottom, and perimeter because the top, bottom and perimeter areas can be referring to the pad portion of a near rectangularish shape on top. In accordance with these embodiments, the total surface area can include the pad and an attachment (e.g., fixation loop) feature which is not accounted for in the top, bottom, and perimeter measurements.

In one embodiment and as previously described, certain exemplary dimensions of the drug delivery component 80 of FIG. 6D can be as follows. The surface area of the anterior or top surface 116 of the drug delivery component 80 (illustrated as the top surface 116 of the encapsulation sheet 114 in FIG. 6D) can be about 8.5 millimeters squared (mm²). The bottom surface area of the pad can include a surface area of about 7.7 mm². The surface area of the perimeter of the pad can be about 5.8 mm². In accordance with these embodiments, the surface area of the entire pad can be about 41 mm². In other embodiments, volume of the entire upper pad can be about 4.0 millimeter cubed or about 3.57 millimeters cubed (mm³).

In certain embodiments, the volume of a pad for drug delivery disclosed herein can vary depending on the one or more therapeutic agents being delivered and the desired rate and duration of elution of the one or more therapeutic agents from the pad. In accordance with these embodiments and as previously described, the drug delivery component 80 of FIG. 6D can be modified to be of a different size and shape to accommodate different drug delivery characteristics (e.g., dose, duration, timing of initial delivery etc.). In another embodiment, the drug delivery component 80 of FIGS. 6A-6D can correspond with the drug delivery component 80 illustrated in FIG. 3B. As such, exemplary dimensions of smaller drug delivery component 80, such as illustrated in FIG. 3A can be as follows. The surface area of the anterior or top surface of the drug delivery component 80 can be about 4.8 millimeters squared (mm²). The bottom surface area of the pad can include a surface area of about 4.0 mm². The surface area of the perimeter of the pad can be about 3.8 mm². Accordingly, the surface area of the pad can be about 25.6 mm². The volume of the entire upper pad can be about 2.02 millimeters cubed (mm³).

Figure 7A:
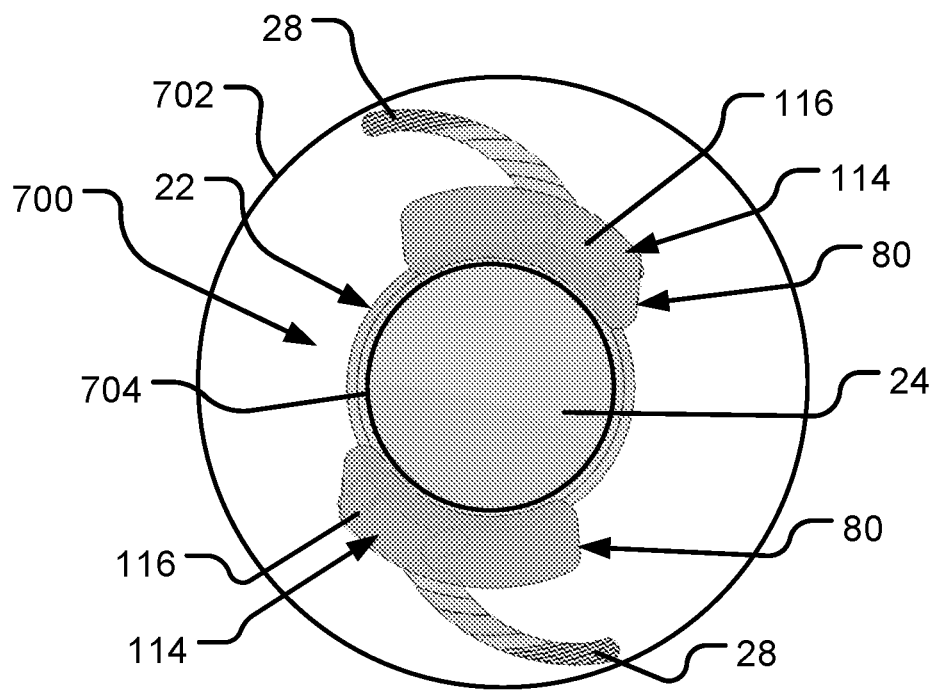
FIGS. 7A and 7B are, respectively, anterior views of an intraocular drug delivery system implanted in the capsular bag with two different sizes of drug delivery components.
Figure 7B:
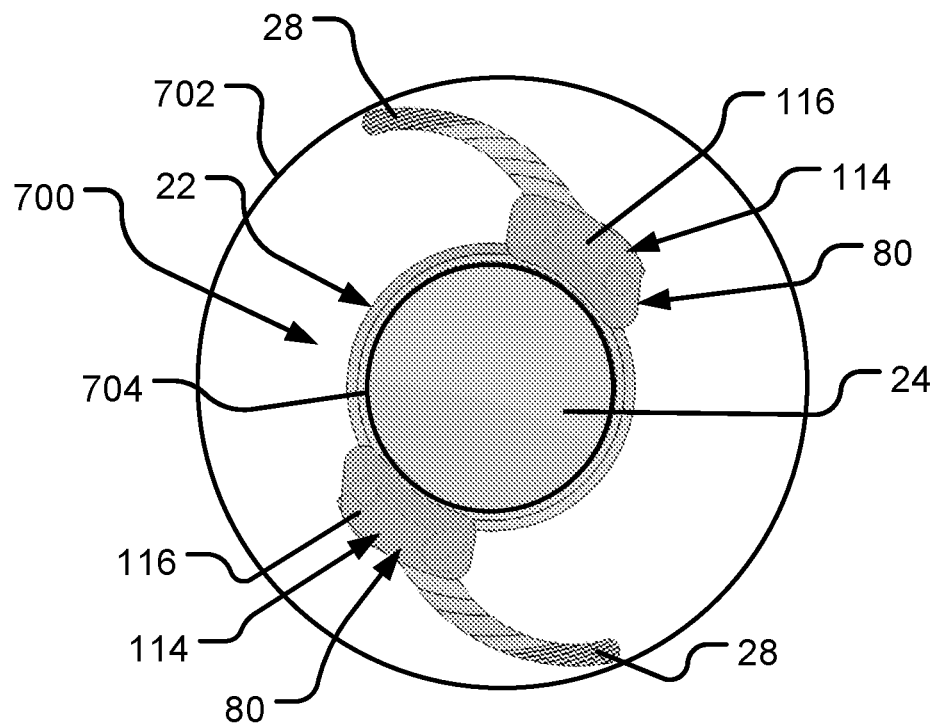

FIGS. 7A and 7B illustrate, respectively, anterior views of an intraocular drug delivery system 700 implanted in the capsular bag 702 with two different sizes of drug delivery components 80. The drug delivery components 80 can be sized and shaped such that they can be positioned within the capsular bag 702 of the eye of a subject (e.g., patient). In some embodiments, the drug delivery system 700 is configured to be affixed to the capsular bag 702. In some aspects, the drug delivery system 700 can be delivered through the capsular bag 702. As illustrated in the FIGS. 7A and 7B, the capsular bag 702 includes an anterior opening 704 formed during surgery to provide an access into the capsular bag 702. The intraocular drug delivery system 700 can be introduced into the eye of a patient, through a small incision at the edge of the cornea, and into the capsular bag 702 via the anterior opening 704. The intraocular drug delivery system 700 can be delivered through the anterior opening 704 via an access cannula (not shown) or otherwise injector. In certain embodiments, the intraocular drug delivery system 700 is flexible such that it can be folded or rolled and subsequently unfolded or unrolled. In some aspects, the drug delivery component 80 can be secured to the lens 24 or otherwise haptic 28 as the intraocular drug delivery system 700 is folded or rolled and/or subsequently unfolded or unrolled. In some examples, the IOL assembly 22 is configured to form a fold such that it can be positioned within an access cannula or otherwise injector while the drug delivery component 80 is secured to the IOL assembly 22 (e.g., secured to the haptic-lens junction). When the IOL assembly 22 is folded (i.e., forming the fold), the drug delivery component 80 can remain secured to the IOL assembly 22 and also remain outside of the fold of the IOL assembly 22. In this way, the drug delivery component 80 is not inhibiting the fold of the IOL assembly 22 and causing it to be bulkier than it would be without the drug delivery component 80. The intraocular drug delivery system 700 can be in a folded orientation within the access cannula. Upon delivery into the capsular bag 702, the intraocular drug delivery system 700 unfurls into the shape shown in FIGS. 7A and 7B, respectively. In each of the figures, the top or anterior surface 116 of the encapsulation sheet 114 of the drug delivery component 80 lies adjacent or opposes an inner surface of an anterior portion of the capsular bag 702. As illustrated in the figures, the lens 24 is generally positioned coaxial with the anterior opening 704 and the haptics 28 extend outwards therefrom towards the interior surface of the capsular bag 704. The haptics 28 generally maintain the position of the system 700 in place within the capsular bag 702 for the lens 24 to function properly. In certain embodiments, when the intraocular drug delivery system 700 is implanted, the drug delivery component 80 is implanted between anterior and posterior capsule surfaces of the eye. In certain embodiments, the intraocular drug delivery system 700 is configured to retain its shape after it is implanted in the capsular bag 702 until after the capsular bag closes onto the intraocular drug delivery system 700.

For initial installation of the intraocular drug delivery system 700, the drug delivery component 80 can be fixed to the IOL assembly 22 prior to insertion of both into the eye, and the assembled system 700 can be folded and passed through the incision in the cornea, through the anterior opening 704, and then released in the capsular bag 702. Alternatively, for initial installation of the intraocular drug delivery system, the drug delivery component 80 can be fixed to the IOL assembly 22 after insertion of the IOL into the eye, by first inserting the IOL through the incision and releasing it in the capsular bag 702, and then inserting the drug delivery component 80 through the incision and manipulating the drug delivery component 80 to slip the fixation portion over the haptic and thereby fix the drug delivery component 80 to the haptic and IOL assembly 22.

As illustrated in FIGS. 7A and 7B, the drug delivery components 80 can be generally positioned within the capsular bag 702 and radially outward of the anterior opening 704. And once positioned within the eye, the drug delivery component 80 elutes the therapeutic agent from within into the capsular bag 702 and to the various anatomical structures within the eye. The therapeutic agent can elute within the capsular bag 702, through the capsular bag 702, and/or through the anterior opening 704 in the capsular bag 702 in order to disperse the therapeutic agent throughout the eye. In certain embodiments, the intraocular drug delivery system 700 is not configured to be placed on a surface of the eye. In these embodiments, after the intraocular drug delivery system 700 is implanted, the intraocular drug delivery system 700 is not in contact with a surface of the eye.

As described previously, the drug delivery component 80, as well as the IOL assembly 22, is non-biodegradable (also described as non-bioerodible). In accordance with embodiments disclosed herein, the shape and structure to both the drug delivery component 80 and the IOL assembly 22 do not change over time as the at least one therapeutic agent, composition and/or formulation of the drug delivery component 80 elutes therefrom.

In some embodiments, a capsular bag 702 of a human eye can have an anterior capsule surface area of about 30 mm$^2$ to about 100 mm$^2$, or about 40 mm$^2$ to about 90 mm$^2$ or about 35 mm$^2$ or about 83 mm$^2$ or about 57 mm$^2$. In certain embodiments, In accordance with these embodiments, each of the drug delivery components 80 illustrated in FIG. 7A can have an anterior surface area of about 8.5 mm$^2$. In certain embodiments, with two drug delivery components 80, a total surface area of about 17.0 mm$^2$ can be configured to lie adjacent to the 80 mm$^2$ anterior capsular bag 704. In this example, about 21% of the anterior capsular surface area can abut a drug delivery component 80. For the drug delivery components 80 illustrated in FIG. 7B, each of the drug delivery components 80 has an anterior surface area of about 4.8 mm$^2$. With two drug delivery components 80, a total surface area of about 9.6 mm$^2$ is configured to lie adjacent the 80 mm$^2$ anterior capsular bag 704. Therefore, about 12% of the anterior capsular surface area can abut a drug delivery component 80. Other examples, depending on the size of the anterior capsule surface area of the human and the size of the drug delivery components can be used.

In certain embodiments, the drug delivery system 700 of FIG. 7A can be sized (e.g., shape, dimensions) and configured (e.g., concentration) for a period of release of the at least one therapeutic agent, formulation and/or composition. For example, the at least one therapeutic agent can have a concentration such that the period of release is about three years to about 10 years. In certain embodiments, the drug delivery system 700 of FIG. 7A is sized and configured for about a three-year release of the therapeutic agent, with a release rate of about 80 to about 150 nanograms (ng) per day (e.g., about 120 ng/day bimatoprost). By decreasing the surface area of the drug delivery component 80, as illustrated in FIG. 7B, the drug delivery system 700 is sized and configured for about a three-year release of the at least one therapeutic agent with a release rate of about 60 ng per day, (e.g., bimatoprost). In certain embodiments, the amount of the therapeutic agent within the polymer matrix can be decreased to provide for a shorter release while still providing for a consistent release rate. In one embodiment, the drug delivery component 80 can deliver the therapeutic agent for about twelve months up to about 10 years or any time in between with a consistent release rate of between about 20 ng/day and 300 ng/day. In certain embodiments, the drug delivery component 80 can deliver the at least one therapeutic agent for between about twelve and about 6 years or any time in between with a consistent release rate of between about 20 ng/day and 300 ng/day. In certain embodiments, the drug delivery component 80 can deliver the at least one therapeutic agent for between about twenty-four and about 3 years with a consistent release rate of between about 20 ng/day and 300 ng/day. In certain embodiments, the drug delivery component 80 can deliver the at least one therapeutic agent for up to ten years or for any predetermined period of time before the drug delivery component 80 needs replacement. In some embodiments, the drug delivery component 80 can deliver the at least one therapeutic agent for up to ten years with a consistent release rate of between about 20 ng/day and 300 ng/day. In some embodiments, the release rate of the at least one therapeutic agent, composition and/or formulation is about 30 ng/day. In certain embodiments, the drug delivery devices disclosed herein reduce waste of agents, over-dosing, toxicity, increase efficacy and/or alleviate the need for compliance of a subject to adhere to a scheduled delivery of the at least one therapeutic agents contemplated herein.

In certain embodiments, the drug delivery system 700 can deliver the at least one therapeutic agent for between about one week up to about one hundred and twenty months (e.g., for a prolonged period) depending on the eye condition and the subject being treated. For example, the concentration of the at least one therapeutic agent can be designed or adapted to provide a predetermined period of time for release of the at least one therapeutic agent to treat the eye of a subject (e.g., patient) to completion or to some desired endpoint or for prolonged, lifelong treatment (e.g., where the drug delivery component is replaced as needed). In certain embodiments, the drug delivery system 700 can deliver the at least one therapeutic agent for between about one week and about ten years. For example, the drug delivery system 700 can deliver the at least one therapeutic agent for at least one year. In certain embodiments, the drug delivery system 700 can deliver the therapeutic agent for at least six months (i.e., six months or longer). In certain embodiments, the drug delivery system 700 can deliver the therapeutic agent for at least three years (i.e., three years or longer). In certain embodiments, the drug delivery system 700 can deliver the therapeutic agent for between six months and about six years. For example, the drug delivery system 700 can deliver the therapeutic agent for about sixty months. In certain embodiments, the drug delivery system 700 can deliver the therapeutic agent for more than seventy-two months.

While the amount or concentration of the at least one therapeutic agent mixed with the polymer can affect the duration of elution (e.g., twelve months, twenty-four months, and thirty-six months, etc.), the thickness of the biocompatible polymer encapsulation layer or shell surrounding the drug-containing component 100 can also affect the initial and/or the eventual elution rate of the at least one therapeutic agent. For example, the elution rate can be determined in part by the thickness of the encapsulation layer while still providing for a near or essentially zero-order or near steady-state release rate of at least one therapeutic agent. In some embodiments, there is no encapsulation layer. In other embodiments there is an encapsulation layer of about 10 to about 500 microns, or about 20 to about 400 microns, or about 30 to about 300 microns or about 50 to about 300 microns. Additionally, the solubility, diffusivity, and/or bioavailability of at least one therapeutic agent, composition and/or formulation embedded or encased in the polymer can affect the elution rate.

It is noted that, in certain embodiments and as previously described (with reference to FIGS. 7A and 7B) the two drug delivery components 80 on the IOL assembly 22 can include different therapeutic agents or mixtures thereof or combinations thereof, such as one embedded within one drug delivery component 80 and one embedded within the other drug delivery component 80. In certain embodiments, each of the drug delivery components 80 can be the same size, as illustrated in FIGS. 7A and 7B; alternatively, the IOL assembly 22 can include two drug delivery components 80 of different sizes on the same assembly. By this example, there can be one drug delivery component 80 with the size illustrated in FIG. 7A and one drug delivery component 80 with the size illustrated in FIG. 7B. In accordance with these embodiments, the at least one therapeutic agent embedded in drug delivery components 80 can have differing concentrations of the at least one therapeutic agent in one drug delivery component 80 compared to the other.

In certain embodiments, the drug delivery system 700 of FIG. 7A can be sized and configured to elute different doses of the at least one therapeutic agents with the same or different total release times. In one embodiment, the at least one therapeutic agents can be configured to each have a release time of about three years up to about 10 years or anything in between. In one embodiment, the at least one therapeutic agent can have a release time of about one week up to about 10 years. In another embodiment, the at least one therapeutic agent can have a release time of at least one week up to about 10 years or each drug delivery component 80 of 2 or more drug delivery component 80 on an IOL can contain the at least one therapeutic agent with differing release date completions from the drug delivery component 80.

In certain embodiments, at least two therapeutic agents (directed to the same or different eye conditions) can be encased in a core of a drug delivery device disclosed herein and have the same or different release rates per day of each therapeutic agent. In certain embodiments, the two therapeutic agents (whether the same or different) can be provided and have release rates of about 2 to about 2000 ng per day or about 2 to about 200 ng per day of each therapeutic agent depending on the agent. In certain embodiments, the at least two therapeutic agents (whether the same or different) can be provided and have release rates of about 30 ng per day of each therapeutic agent or have different release rates depending on the condition being treated.

While the drug delivery system 700 is described as being implanted in the capsular bag 702 of the eye, the system 700 described herein (with or without an optic/lens) can be delivered into other regions of the eye such as the sulcus or ciliary sulcus. In other embodiments, the drug delivery component 80 described herein can be attached to other systems such as the sulcus implant/drug delivery platform illustrated and described in PCT/US2021/057104, filed Oct. 28, 2021, which is hereby incorporated by reference in its entirety for all purposes, to deliver active agents at constant rates to the eye. Such devices can be supported in the sulcus, as illustrated in FIG. 2 of PCT/US2021/057104.

In certain embodiments, kits are provided. In some embodiments, a kit can include the drug delivery component 80 and instructions for use. In some aspects, the kit can include drug delivery system 700. In some aspects, the kit can include packaging for storing and/or shipping the drug delivery component 80 and/or the drug delivery system 700. In certain aspects, the kit can include a system to secure the drug delivery component 80 to a lens 24 or otherwise haptic 28.

Figure 8:
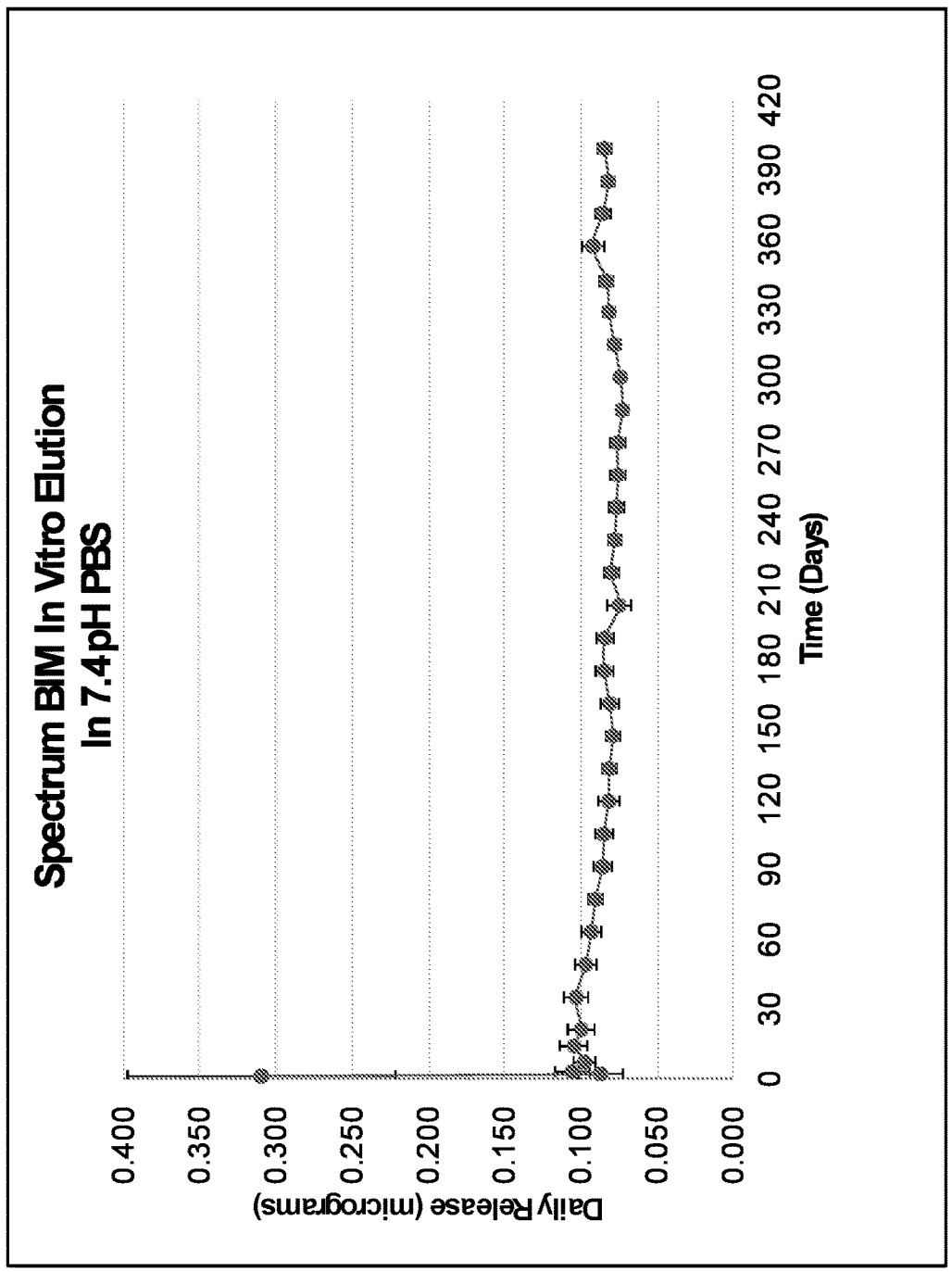
FIG. 8 is an exemplary graph of daily release or elution of a pharmaceutical or therapeutic agent in vitro versus time.

As illustrated in FIG. 8, which is a graph 800 of daily release or elution (in micrograms) of Bimatoprost in vitro versus time (day), the release rate over a four-hundred-day study is essentially a zero-order and/or a steady state elution rate. The target release rate in this study on rabbits was 0.050 to 0.100 micrograms per day. As illustrated in FIG. 8, the average release rate is slightly less than 0.100 micrograms per day with a range of about 0.075 micrograms to about 0.100 micrograms. The graph supports a zero-order release, which indicates that there is a consistent amount of drug released per unit time over a given duration.

Figure 9:
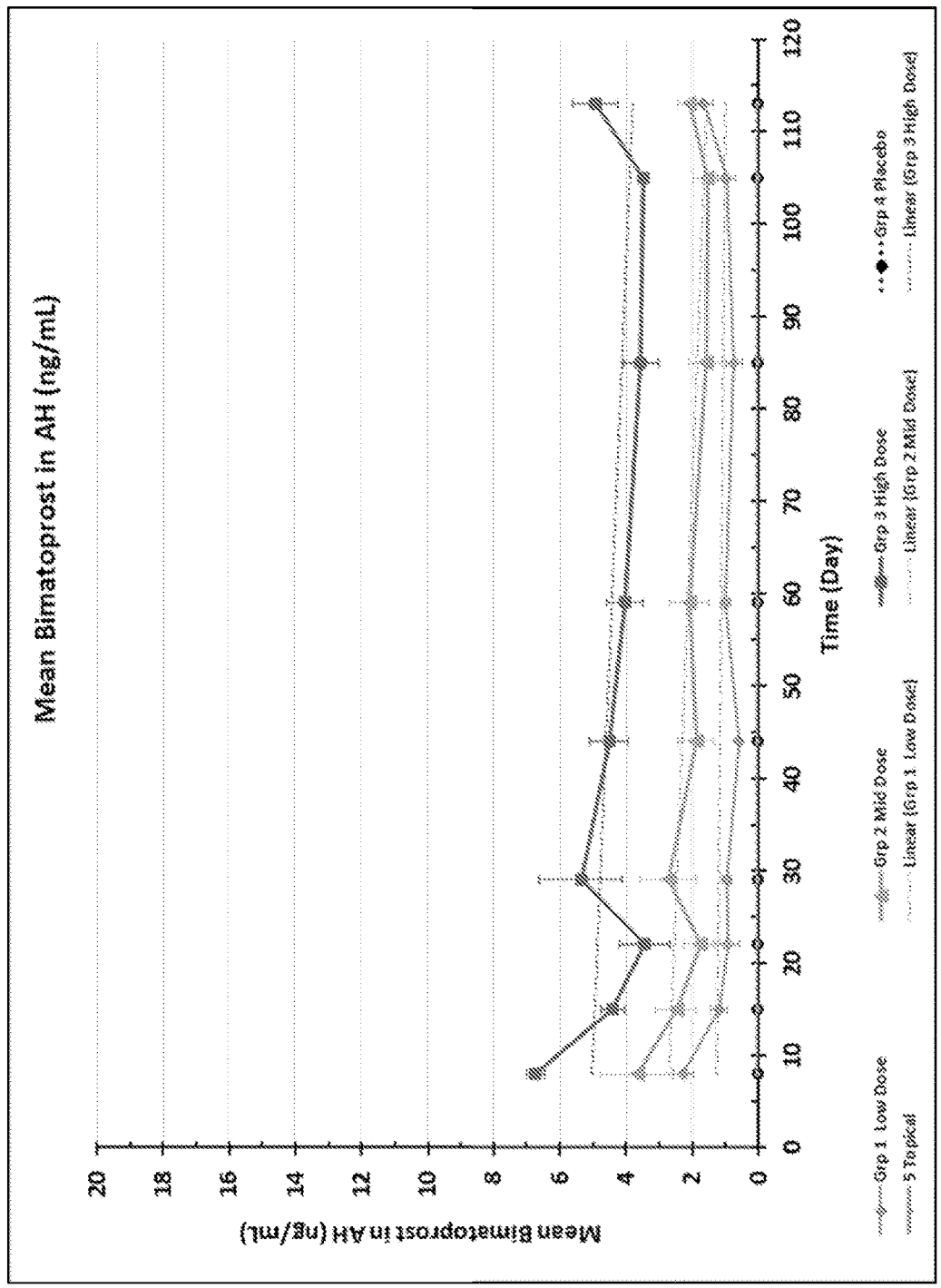
FIG. 9 is an exemplary graph of a therapeutic agent delivered to the aqueous humor of an eye of canines versus time.

As illustrated in FIG. 9, which is a graph 900 of an example of a therapeutic agent disclosed herein, Bimatoprost, sampled in the aqueous humor (ng/mL) over time (days), various doses were tested, for example in dogs. In this example, there was a low dose group of dogs (Grp 1), a mid-dose group of dogs (Grp 2), a high dose group of dogs (Grp 3), and a placebo group of dogs (Grp 4). The placebo or control group (Grp 2) exhibited zero Bimatoprost ng/ml. The mean measurements of Bimatoprost in the aqueous humor of the other groups increased with the higher doses provided to the dogs. As found with the low dose group (Grp 1), the mid-dose group (Grp 2), and the high dose group (Grp 3), the level of Bimatoprost in the aqueous humor exhibited a zero-order elution rate over the study period of about one hundred thirteen days.

In certain embodiments, when an originally implanted drug delivery component 80 is depleted and/or no longer providing a therapeutic dose, either by elution or bio-erosion, a subsequent surgical procedure can be performed in which a surgeon removes the original drug delivery component, making another incision at the border of the cornea to insert and attach a new drug delivery component to the haptic and IOL assembly using a grasping tool. The removal of the original drug delivery component and replacement with a new drug delivery component can be performed, for example, after the original therapeutic agent of the drug delivery component is exhausted or depleted, or whenever it is desired to replace the original drug delivery component with a new drug delivery component which contains a replenished or different therapeutic agent, and can be performed after the incision made to implant the original drug delivery component has healed, and thus requires making a new incision. During the surgical procedure, if necessary, the surgeon can insert a grasping tool to remove the original drug delivery component from the haptic and IOL assembly, and remove it from the eye, and insert a new drug delivery component and use the grasping tool to manipulate the new drug delivery component to slip it over the haptic and thereby secure it to the IOL assembly. In certain embodiment, the new drug delivery component can be added onto either an IOL in the bag or an IOL in the sulcus.

In the following paragraphs, numerous embodiments are disclosed. In one embodiment, a drug delivery matrix is disclosed for use in an eye of a subject, the drug delivery matrix having: a polymer core having a non-bioerodible, non-biodegradable, polymer and one or more pharmaceutical agent(s) intermixed therein; and a non-bioerodible, non-biodegradable, polymer membrane surrounding the polymer core wherein the non-bioerodible, non-biodegradable, polymer membrane controls an elution rate of the one or more pharmaceutical agent(s) from the non-bioerodible, non-biodegradable, polymer into an environment outside of the non-bioerodible, non-biodegradable, polymer membrane. In accordance with these embodiments, the drug delivery matrix can include one or more pharmaceutical agent(s) for example, one or more of an amorphous solid, a crystalline, microparticle, spray-dried compound or agent, and a lyophilized pharmaceutical agent(s) or a combination thereof. In other embodiments, the one or more pharmaceutical agent(s) is soluble in the non-erodible, non-biodegradable, polymer of the polymer core.

In certain embodiments, the drug delivery matrix can be in the shape of a rectangular pad, square pad, a flat configuration, a slab, a block, a sphere, or a cylinder. In other embodiments, the drug delivery matrix includes at least one drug delivery rectangular pad, square pad, block, or slab associated with a haptic of an intraocular lens (IOL). In yet other embodiments, the at least one drug delivery rectangular pad, square pad, block, or slab is associated with a haptic-optic junction of the IOL. In some embodiments, the drug delivery component having a polymer core is non-refillable. In certain embodiments, the drug delivery matrix has a neutral refractive index or is devoid of a refractive index. In other embodiments, the drug delivery matrix is conformed to be positioned in a capsular bag of an eye. In accordance with these embodiments, the drug delivery matrix is conformed in shape and size to be positioned in the capsular bag of the eye.

In some embodiments, the drug delivery matrix can include an implant body having a scaffold, the implant body being associated with the drug delivery matrix. In some embodiments, a haptic of devices disclosed herein extends outwardly from the scaffold.

In certain embodiments, the drug delivery matrix or drug delivery component can be a preservative free drug delivery matrix or component. In some embodiments, the polymer core can be configured to contain a concentration of one or more pharmaceutical agent(s) or therapeutic agents for storing for at least three months storage and then delivery of the one or more pharmaceutical agent(s) or therapeutic agents to a subject treat the subject for an eye condition. In certain embodiments, the polymer core is configured to contain a concentration of the one or more pharmaceutical agent(s) or at least one therapeutic agents for at least one year of storage and delivery of the one or more pharmaceutical agent(s) to a subject to treat the subject for an eye condition. In accordance with these embodiments, drug delivery component 100 and/or drug delivery component 80 can be stored for prolonged periods either individually or in groups (e.g., in individual wraps or packages or stacked and packaged) for later introduction to an eye device and/or IOL contemplated herein.

In certain embodiments, the drug delivery component 80 can include at least one of a polymer core and the non-bioerodible, non-biodegradable, polymer the at least one of the polymer core and the non-bioerodible, non-biodegradable, polymer membrane can be made up of one or more of silicone, polyurethane, polyethylene, polyvinyl acetate, polyethylene glycol, polymethacrylate, polystyrene, or polytetrafluoroethylene. In certain embodiments, the at least one of the polymer core and the non-bioerodible, non-biodegradable, polymer membrane is made up of silicone or a mixture of silicones. In other embodiments, the drug delivery matrix can include a crosslinked polymer. In certain embodiments, a polymer or crosslinked polymer of use herein can have a molecular weight cut-off of about 5,000 to about 250,000 mw or about 10,000 to about 200,000. In certain embodiments, the non-bioerodible, non-biodegradable, polymer is a biocompatible polymer. In some embodiments, the non-bioerodible, non-biodegradable, polymer membrane includes a non-porous polymer membrane or a consistent or uniform membrane devoid of pores or a membrane devoid of holes. In accordance with these embodiments, this uniform membrane can permit the uniform distribution of the at least one therapeutic agent to a subject's eye. In certain embodiments, the non-bioerodible, non-biodegradable, polymer is a solid matrix with the one or more pharmaceutical agent(s) intermixed therein. In other embodiments, the solid matrix retains its shape upon elution of the one or more pharmaceutical agent(s) or at least one therapeutic agent intermixed therein.

In certain embodiments and further to the paragraphs above, a drug delivery matrix of an IOL contemplated herein is not configured to be placed on a surface of an eye.

In some embodiments and further to the paragraphs above, pharmaceutical agent(s) of use in a drug delivery component disclosed herein can include, but is not limited to, one or more of a protein, polypeptide, polynucleotide, carbohydrate, fatty acid, a small molecule, and/or an aptamer of use to treat an eye condition or for delivery of a therapeutic through a component or matrix. In some embodiments, the at least one therapeutic agent can include, but is not limited to, an agent that lowers intraocular pressure, an antibiotic, an anti-inflammatory agent, a chemotherapeutic agent, an agent that promotes nerve regeneration, a steroid, an anti-oxidant, an anti-proliferative agent, an anti-mitotic agent, or a pharmaceutically acceptable salt thereof, or any combination thereof. In some embodiments, the one or more pharmaceutical agent(s) can include, but is not limited to, one or more of a beta blocker, alpha agonists, an antibiotic, a chemotherapeutic agent, a prostaglandin analog, rho kinase inhibitors such as rho-associated protein kinase inhibitor or ROCK inhibitor (e.g., ROCK1 (ROKβ) and ROCK2 (ROKα)), a tyrosine kinase inhibitor (TKI), a carbonic anhydrase inhibitor, a steroid, glucocorticoid, NSAIDs, anti-fibrotic agent, an anti-oxidant, an anti-mitotic agent, a miotic agent, a mydriatic agent, an anti-neoplastic agent, a 11β-Prostaglandin F2α or a 11-epi-PGF2α agent, an antibody, other agent that lowers intraocular pressure, an agent that promotes nerve regeneration, an anti-inflammatory agent, an anti-autoimmune agent, and any combination thereof. In certain embodiments, a pharmaceutical or therapeutic agent disclosed herein can include, but is not limited to, one or more of travoprost, latanoprost, tafluprost, timolol, bimatoprost, brimonidine, brinzolamide, aflibercept, bevacizumab, pilocarpine, ethacrynic acid, CNP/BNP/ANP, tetrahydrocannabinol (THC), pegaptanib, ranibizumab, methotrexate, dexamethasone, triamcinolone, ketorolac, dorzolamide, prednisolone, cannabidiol (CBD), cannabinoids or other molecules derived from a *cannabis* plant, or other agents used to treat glaucoma, macular degeneration, or other ocular condition for a short or prolonged period. In certain embodiments, the pharmaceutical agent(s) can include, but is not limited to, one or more of bimatoprost and dexamethasone.

In certain embodiments, the pharmaceutical agent(s) or at least one therapeutic agent can contain a liquid or water content equal to, or less than about 5.0%, 4.0%, 3.0%, 2.0%, 1.0%, or about 0.05%. In some embodiments, at least one pharmaceutical agent or at least one therapeutic agent or formulation or composition disclosed herein can include a particle size of less than or equal to about 50 μm, 45 μm, 40 μm, 30 μm, 25 μm, 20 μm, or 15 μm.

In some embodiments, the drug delivery matrix or drug delivery component can be associated with an intraocular lens (IOL). In certain embodiments, the drug delivery matrix or drug delivery component is associated with an intraocular lens (IOL). In some embodiments the drug delivery matrix is configured to be secured to the IOL. In some embodiments, the IOL includes, but is not limited to, a lens and a haptic extending outwards from the lens at a lens-haptic junction, where the IOL is configured to form a fold for positioning within an injector, and when the IOL forms the fold, the drug delivery matrix can be configured to be secured to the haptic-lens junction while remaining outside the fold.

In some embodiments, kits are contemplated. In accordance with these embodiments, a kit can include any of the devices disclosed herein and instructions for use. In other embodiments, kits can include a drug delivery component or a drug delivery matrix. In certain embodiments, kits can include an IOL for use with the drug delivery matrix. Kits further include packaging for the drug delivery matrix. In some embodiments, kits can include a system to affix the drug delivery matrix to the IOL.

In other embodiments, methods for delivering at least one therapeutic agent using a device disclosed herein to an eye of a subject are disclosed. In certain embodiments, methods include, but are not limited to, implanting a drug delivery component into the eye and adjacent to a fluid-permeable membrane of the eye of the subject, the drug delivery component including a solid drug core and a solid non-bioerodible membrane encapsulating the solid drug core, the solid drug core including at least one therapeutic agent embedded within a biocompatible polymer, the at least one therapeutic agent situated or embedded in a manner to elute from the solid drug core through the solid non-bioerodible membrane and into the eye; and delivering a therapeutically effective amount of the at least one therapeutic agent to the eye. In certain embodiments, delivery of the at least one therapeutic agent is for about 1 week up to about 10 years or for at least about six months. In other embodiments, the fluid-permeable membrane is a capsular bag of the eye, and the drug delivery component is implanted in the capsular bag of the eye. In some embodiments, the at least one therapeutic agent is delivered through the capsular bag of the eye. In yet other embodiments, the therapeutically effective amount of the at least one therapeutic agent can be delivered at a sustained release rate.

In other embodiments and further to the paragraphs above devices and methods disclosed herein include, supporting a position of the drug delivery component within the eye and adjacent the fluid-permeable membrane of the eye of the subject. In some embodiments, the drug delivery component is supported in the position via an intraocular lens (IOL). In yet other embodiments, the IOL can further include a haptic, and the drug delivery component includes an aperture that receives the haptic therethrough. In other embodiments, methods include contacting an inner surface of the fluid-permeable membrane with a portion of the drug delivery component; optionally, the portion of the drug delivery component having a surface area of greater than 4 mm$^2$. In accordance with these methods, the drug delivery component includes a pad. In some embodiments, the drug delivery component includes an attachment structure coupled to the pad, the drug delivery component configured to couple to an intraocular lens via the attachment structure.

In certain embodiments, upon insertion of a device disclosed herein, a fluid-permeable membrane for implantation can include a capsular bag of the eye, and the drug delivery component can be configured to retain its shape from implantation until after the capsular bag closes onto the drug delivery component disclosed herein.

In some embodiments, the fluid-permeable membrane includes a capsular bag of the eye, and the drug delivery component is positioned outside the capsular bag and at least partially supported by a scaffold in a sulcus of the eye. In certain embodiments, the scaffold includes an intraocular lens. In other embodiments, the drug delivery component is implanted between anterior and posterior capsule surfaces of the eye.

In some embodiments and further to the paragraphs above, implanting the drug delivery component into the eye can include injecting the drug delivery component into the eye via an injector, where the drug delivery component transitions from a folded orientation in the injector to an unfolded orientation in the eye.

In some embodiments, an intraocular implant for implantation within an eye of a subject, can include, but is not limited to, an implant body including a scaffold and at least one haptic extending outwards from the scaffold, the at least one haptic configured to support a position of the implant body within the eye; and a drug delivery component configured to couple to the implant body, the drug delivery component comprising a solid drug core and a solid non-bioerodible membrane encapsulating the solid drug core, the solid drug core comprising at least one therapeutic agent embedded within a biocompatible polymer. In some embodiments, the drug delivery component can further include an attachment structure coupled to the solid non-bioerodible membrane, the attachment structure configured to facilitate attachment to the implant body. In other embodiments, the attachment structure can include an aperture configured to receive a haptic of the at least one haptic therethrough. In yet other embodiments, the solid non-bioerodible membrane is configured to control a rate of elution of the at least one therapeutic agent. In some embodiments, the rate of elution is a constant daily release rate. In other embodiments, the solid non-bioerodible membrane can have a thickness of about 15.0 microns to about 3.0 mm. In other embodiments, the solid non-bioerodible membrane includes a thickness of up to about 3.0 mm. In yet other embodiments, the solid drug core and the solid non-bioerodible membrane can be formed in a pad having generally planar top and bottom surfaces. In certain embodiments, the scaffold contemplated herein can include a lens positioned therein.

In some embodiments and as previously described, the at least one haptic can include a first haptic and a second haptic, the first and second haptics configured to retain a position of the intraocular implant within a capsular bag of the eye. Alternatively, in other embodiments, the at least one haptic can include a first haptic and a second haptic, the first and second haptics configured to retain a position of the intraocular implant within a ciliary sulcus of the eye. In certain embodiments, the at least one therapeutic agent can include, but is not limited to, an agent that lowers intraocular pressure, an antibiotic, an anti-inflammatory agent, a chemotherapeutic agent, an agent that promotes nerve regeneration, a steroid, an anti-oxidant, an anti-proliferative agent, an anti-mitotic agent, an aptamer, a complement factor, an antibody, or a pharmaceutically acceptable salt thereof, or any combination thereof.

While the preferred embodiments of the devices and methods have been described in reference to the environment in which they were developed, they are merely illustrative of the principles of the inventions. The elements of the various embodiments can be incorporated into each of the other species to obtain the benefits of those elements in combination with such other species, and the various beneficial features can be employed in embodiments alone or in combination with each other. Other embodiments and configurations can be devised without departing from the spirit of the inventions and the scope of the appended claims.

What is claimed is:

1. An intraocular implant for implantation within an eye of a subject, the intraocular implant comprising:
   an implant body including a scaffold and at least one haptic extending outwardly from the scaffold, the at least one haptic configured to support a position of the implant body within the eye; and
   a drug delivery component configured to couple to the implant body, the drug delivery component comprising a core and a solid non-bioerodible membrane fully encapsulating the core, the core comprising at least one therapeutic agent embedded within a biocompatible, non-bioerodible polymer, the solid non-bioerodible membrane is configured to permit and control a rate of elution of the at least one therapeutic agent from the core through the solid non-bioerodible membrane by diffusion.

2. The intraocular implant of claim 1, wherein the drug delivery component further comprises an attachment structure coupled to the solid non-bioerodible membrane, the attachment structure configured to facilitate attachment to the implant body.

3. The intraocular implant of claim 2, wherein the attachment structure comprises an aperture configured to receive a haptic of the at least one haptic therethrough.

4. The intraocular implant of claim 1, wherein the rate of elution is a fixed or constant daily release rate.

5. The intraocular implant of claim 1, wherein the solid non-bioerodible membrane comprises a thickness of about 15.0 microns to about 2.0 mm.

6. The intraocular implant of claim 1, wherein the solid non-bioerodible membrane comprises a thickness of up to 1.0 mm.

7. The intraocular implant of claim 1, wherein the core and the solid non-bioerodible membrane are formed into a pad having generally planar top and bottom surfaces.

8. The intraocular implant of claim 1, wherein the scaffold includes a lens positioned therein.

9. The intraocular implant of claim 1, wherein the at least one haptic comprises a first haptic and a second haptic, the first and second haptics configured to retain a position of the intraocular implant within a capsular bag of the eye.

10. The intraocular implant of claim 1, wherein the at least one haptic comprises a first haptic and a second haptic, the first and second haptics configured to retain a position of the intraocular implant within a ciliary sulcus of the eye.

11. The intraocular implant of claim 1, wherein the at least one therapeutic agent comprises at least one of, an agent that lowers intraocular pressure, an antibiotic, an anti-inflammatory agent, a chemotherapeutic agent, an agent that promotes nerve regeneration, a steroid, an anti-oxidant, an anti-proliferative agent, an anti-mitotic agent, an aptamer, a complement factor, an antibody, or a pharmaceutically acceptable salt thereof, or any combination thereof.

12. The intraocular implant of claim 1, wherein the at least one therapeutic agent comprises at least one of, a prostaglandin analogue, an alpha agonist, a rho kinase inhibitor, a tyrosine kinase inhibitor, an adenosine receptor agonist, a carbonic anhydrase inhibitor, an adrenergic and/or a cholinergic receptor activating agent, a beta blocker, or a combination thereof.

13. The intraocular implant of claim 1, wherein the at least one therapeutic agent comprises at least one of, bimatoprost, brimonidine, latanoprost, travoprost, timolol, tafluprost, pilocarpine, brinzolamide, aflibercept, bevacizumab, pilocarpine, ethacrynic acid, CNP/BNP/ANP, tetrahydrocannabinol (THC), pegaptanib, ranibizumab, methotrexate, dexamethasone, triamcinolone, ketorolac, dorzolamide, prednisolone, cannabidiol (CBD), cannabinoids or other molecules derived from a *cannabis* plant, or other agents used to treat glaucoma, macular degeneration, or another ocular condition, or a combination thereof.

14. The intraocular implant of claim 1, wherein the at least one therapeutic agent is bimatoprost, or a pharmaceutically acceptable salt thereof, or derivative thereof.

15. The intraocular implant of claim 1, wherein the core is a solid core.

16. The intraocular implant of claim 1, wherein the core comprises a liquid composition.

17. A kit comprising:
   the intraocular implant according to claim 1; and
   at least one container.

18. The kit according to claim 17, further comprising packaging for the intraocular implant.

19. The kit according to claim 18, further comprising a system to affix the drug delivery component to the implant body of the intraocular implant.

20. A method of implanting an intraocular implant into an eye of a subject comprising: implanting the intraocular implant of claim 1 into the eye of the subject.

21. The intraocular implant of claim 1, wherein the core is solid, and a shape of the core remains intact after eluting the at least one therapeutic agent from the core in the eye of a subject.

22. The intraocular implant of claim 1, wherein the solid non-bioerodible membrane is devoid of pores that are larger than those existing during manufacturing of a solid sheet of the solid non-bioerodible membrane.

23. The intraocular implant of claim 1, wherein perforations for drug elution are not introduced to the solid non-bioerodible membrane during or after manufacturing of a solid sheet of the solid non-bioerodible membrane.

* * * * *